(12) United States Patent
Mazar et al.

(10) Patent No.: US 9,084,583 B2
(45) Date of Patent: Jul. 21, 2015

(54) MEDICAL DEVICE WITH AUTOMATIC START-UP UPON CONTACT TO PATIENT TISSUE

(71) Applicant: Medtronic Monitoring, Inc., San Jose, CA (US)

(72) Inventors: Scott T. Mazar, Woodbury, MN (US); Mark J. Bly, Falcon Heights, MN (US); Arthur Lai, Minnteonka, MN (US)

(73) Assignee: MEDTRONIC MONITORING, INC., San Jose, CA (US)

( * ) Notice: Subject to any disclaimer, the term of this patent is extended or adjusted under 35 U.S.C. 154(b) by 0 days.

(21) Appl. No.: 14/494,165

(22) Filed: Sep. 23, 2014

(65) Prior Publication Data
US 2015/0073251 A1  Mar. 12, 2015

Related U.S. Application Data

(63) Continuation of application No. 12/209,276, filed on Sep. 12, 2008, now Pat. No. 8,897,868.

(60) Provisional application No. 61/055,666, filed on May 23, 2008, provisional application No. 61/046,196, filed on Apr. 18, 2008, provisional application No. 60/972,537, filed on Sep. 14, 2007, provisional application No. 60/972,336, filed on Sep. 14, 2007.

(51) Int. Cl.
| | |
|---|---|
| A61B 5/04 | (2006.01) |
| A61B 5/00 | (2006.01) |
| A61N 1/36 | (2006.01) |
| A61B 5/0402 | (2006.01) |
| A61B 5/053 | (2006.01) |
| A61B 18/18 | (2006.01) |

(52) U.S. Cl.
CPC .............. *A61B 5/6843* (2013.01); *A61B 5/0402* (2013.01); *A61B 5/0531* (2013.01); *A61B 5/6832* (2013.01); *A61N 1/36125* (2013.01); *A61N 1/36139* (2013.01)

(58) Field of Classification Search
CPC .... A61B 5/053; A61B 5/0531; A61B 5/6843; A61B 2017/00026; A61N 1/0484
USPC ................ 600/300, 301, 372, 382, 384, 386, 600/388–393, 544–547; 606/42, 44; 607/115
See application file for complete search history.

(56) References Cited

U.S. PATENT DOCUMENTS 4,599,523 A * 7/1986 Pless et al. ...................... 307/31
5,247,939 A * 9/1993 Sjoquist et al. ................ 600/510

(Continued)

FOREIGN PATENT DOCUMENTS

| EP | 1 575 010 A1 | 9/2005 |
| WO | WO 00/17615 A2 | 3/2000 |
| WO | WO 02/00111 | 1/2002 |

OTHER PUBLICATIONS

Extended European Search Report for corresponding EP Application No. 08830920.8 mailed on Mar. 2, 2015.

*Primary Examiner* — Joseph Stoklosa
*Assistant Examiner* — Brian M Antiskay
(74) *Attorney, Agent, or Firm* — Billion & Armitage; Michael A. Collins

(57) ABSTRACT

Methods and devices for monitoring and/or treating patients comprise a switch to automatically start-up the device when the device contacts tissue. By automatically starting up the device, the device may be installed without the clinician and/or user turning on the device, such that the device can be easy to use. In many embodiments, the device comprises startup circuitry with very low current and/or power consumption, for example less than 100 pA. The startup circuitry can detect tissue contact and turn on circuitry that is used to monitor or treat the patient.

15 Claims, 16 Drawing Sheets

(56) References Cited

U.S. PATENT DOCUMENTS

| | | |
|---|---|---|
| 6,528,960 B1 * | 3/2003 | Roden et al. ............. 318/400.32 |
| 6,580,942 B1 * | 6/2003 | Willshire ....................... 600/509 |
| 8,343,644 B2 * | 1/2013 | Vaisnys et al. ................. 429/90 |
| 2004/0181164 A1 * | 9/2004 | Smith et al. ................... 600/547 |
| 2006/0155354 A1 | 7/2006 | Heath |
| 2007/0100666 A1 | 5/2007 | Stivoric et al. |
| 2007/0270678 A1 * | 11/2007 | Fadem et al. ................. 600/372 |

\* cited by examiner

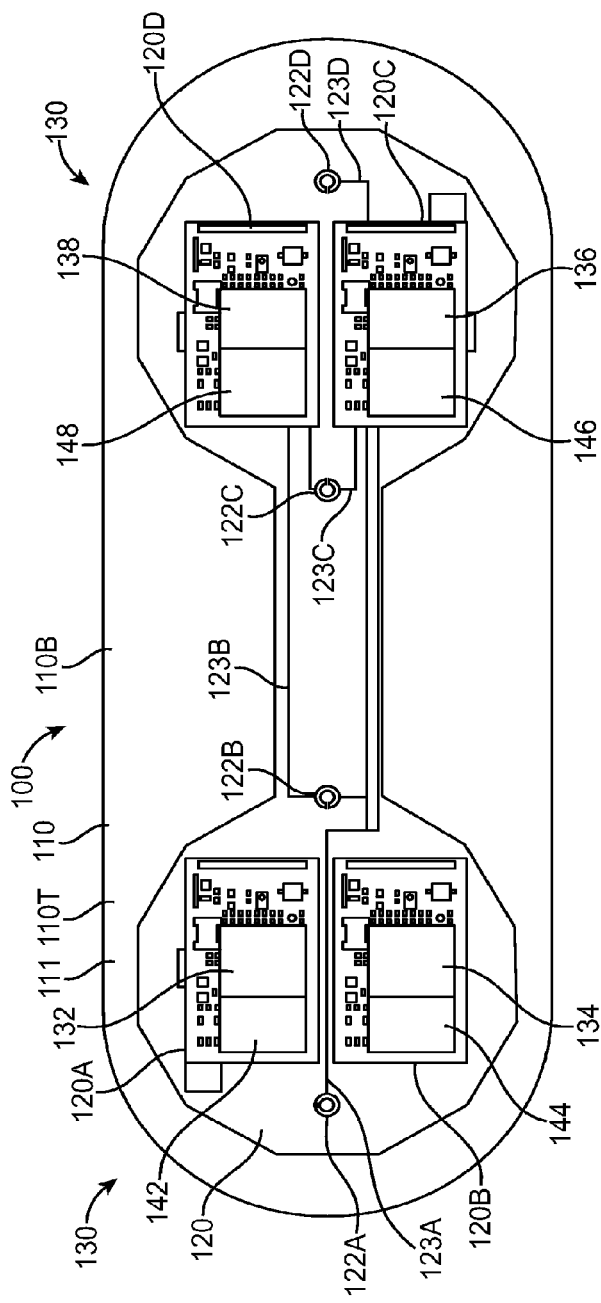
FIG. 1D
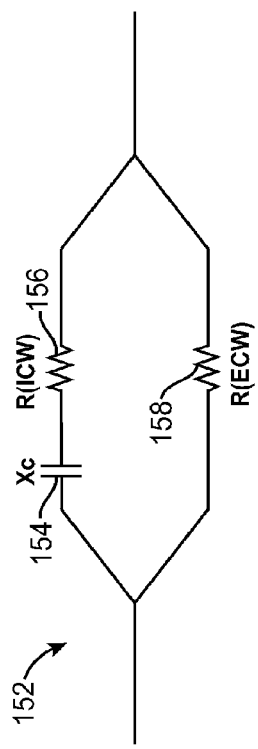
FIG. 1D1

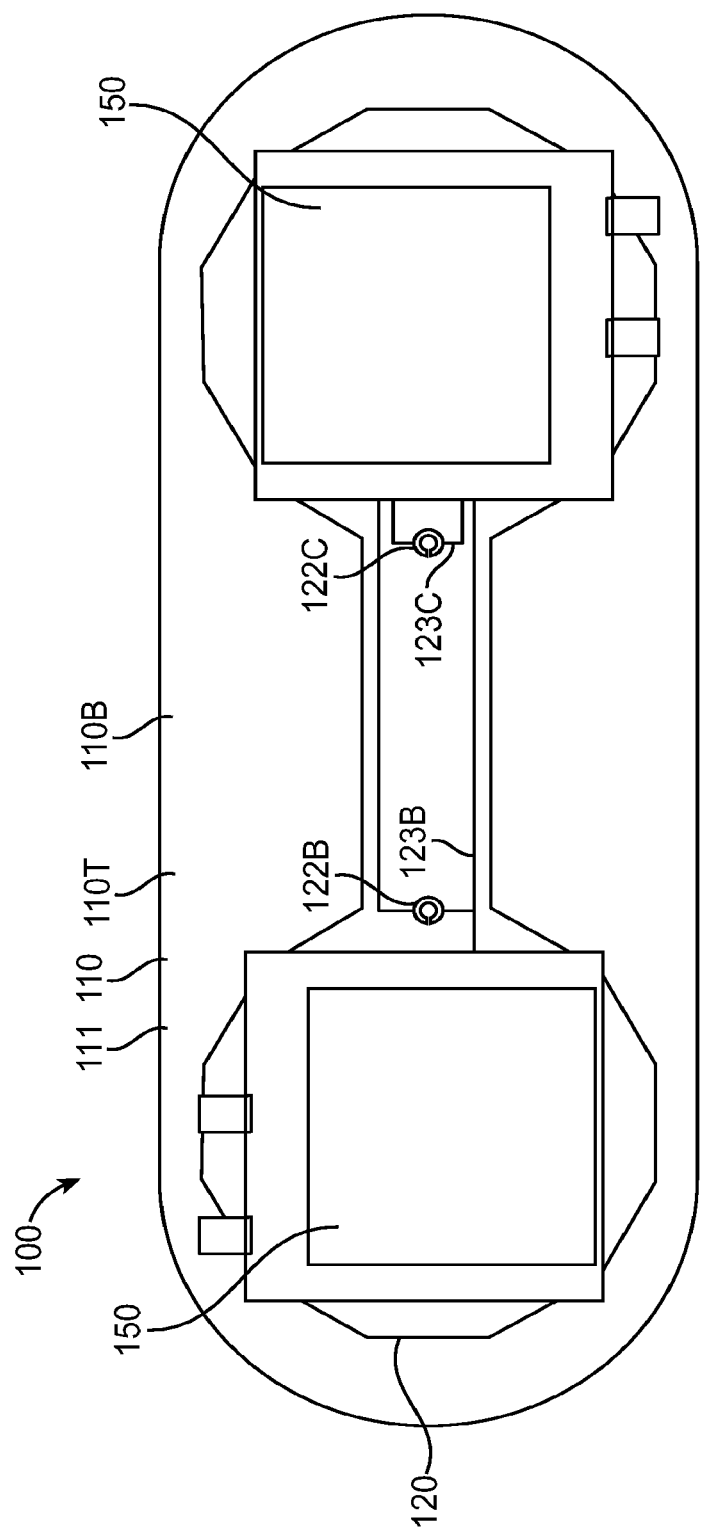

MEDICAL DEVICE WITH AUTOMATIC START-UP UPON CONTACT TO PATIENT TISSUE

CROSS-REFERENCES TO RELATED APPLICATIONS

The present application is a Continuation of U.S. Application No. 12/209,276, filed on Sep. 12, 2008, which claims the benefit under 35 USC 119(e) of U.S. Provisional Application Nos. 60/972,537 and 60/972,336 both filed Sep. 14, 2007, 61/046,196 filed Apr. 18, 2008, and 61/055,666 filed May 23, 2008; the full disclosures of which are incorporated herein by reference in their entirety. A claim of priority to all is made.

The subject matter of the present application is related to the following applications: 60/972,512; 60/972,329; 60/972,354; 60/972,616; 60/972,363; 60/972,343; 60/972,581; 60/972,629; 60/972,316; 60/972,333; 60/972,359; 60/972,340 all of which were filed on Sep. 14, 2007; 61/047,875 filed Apr. 25, 2008; 61/055,645, 61/055,656, 61/055,662 all filed May 23, 2008; and 61/079,746 filed Jul. 10, 2008.

BACKGROUND OF THE INVENTION

1. Field of the Invention

The present invention relates to patient monitoring and/or treatment. Although embodiments make specific reference to monitoring impedance and electrocardiogram signals with electrodes, the system methods and device described herein may be applicable to many applications in which patient monitoring and/or treatment is used, for example long physiological monitoring and/or treatment with implantable devices.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device. In addition to measuring heart signals with electrocardiograms, known physiologic measurements include impedance measurements that can be used to assess the status of the patient. Patients who have sufficiently compromised status may be treated with implantable devices, such as pacemakers, that can provide therapy with electrical pulses delivered through electrodes.

Although current methodologies have been somewhat successful in monitoring and/or treating patients, work in relation to embodiments of the present invention suggests that known methods and apparatus may be less than ideal. In at least some instances, devices for patient monitoring and/or therapy can be expensive, such that some patients do not have access to the these treatments and/or therapies. Also, some of the devices for monitoring and/or treating patients can be complex, such that proper use of the device may be complicated and/or time consuming and may place a burden on the health care provider. In some instances, devices may be complex for a patient to install, such that mistakes may be made and some patients may not be able to use the devices properly for long term at home monitoring.

Therefore, a need exists for improved patient monitoring. Ideally, such improved patient monitoring would avoid at least some of the short-comings of the present methods and devices.

2. Description of the Background Art

The following U.S. patents and Publications may describe relevant background art: U.S. Pat. Nos. 4,121,573; 4,498,479; 4,955,381; 4,981,139; 5,080,099; 5,353,793; 5,511,553; 5,544,661; 5,558,638; 5,673,704; 5,724,025; 5,772,586; 5,836,990; 5,862,802; 5,935,079; 5,949,636; 6,047,203; 6,117,077; 6,129,744; 6,225,901; 6,385,473; 6,416,471; 6,454,707; 6,527,711; 6,527,729; 6,551,252; 6,569,160; 6,595,927; 6,595,929; 6,605,038; 6,645,153; 6,821,249; 6,824,515; 6,980,851; 7,020,508; 7,027,862; 7,054,679; 7,153,262; 2003/0092975; 2004/0243018; 2005/0113703; 2005/0131288; 2006/0010090; 2006/0020218; 2006/0031102; 2006/0089679; 2006/122474; 2006/0155183; 2006/0224051; 2006/0264730; 2007/0021678; 2007/0038038; and 2007/0038078.

SUMMARY OF THE INVENTION

The present invention relates to patient monitoring and/or treatment. Although embodiments make specific reference to monitoring impedance and electrocardiogram signals with electrodes, the system methods and device described herein may be applicable to many applications in which patient monitoring and/or treatment is used, for example long physiological monitoring and/or treatment with implantable devices. Embodiments of the present invention comprise methods and devices for monitoring and/or treating patients, in which the device comprises a switch to automatically start-up the device when the device contacts tissue. By automatically starting up the device, the device may be installed without the clinician and/or user turning on the device, such that the device can be easy to use. In many embodiments, the device comprises startup circuitry with very low current and/or power consumption, for example less than 100 pA. The startup circuitry can detect tissue contact when the device is coupled to tissue and turn on circuitry that is used to at least one of monitor or treat the patient. The very low current used by the start-up circuitry can allow for a long shelf life, such that the device may be shipped from the factory to the end user ready for use with batteries installed. The device may comprise a removable liner having an impedance greater than tissue, for example skin, which can protect an underlying gel or electrodes from degradation and minimize false starts. The device may also comprise a breathable support extending between the at least two electrodes with an impedance that is substantially greater than skin, so as to minimize false starts due to coupling between the electrodes from the breathable support. The liner can be removed to expose the gel pads or the electrodes for placement against the tissue, for example skin, to automatically start the device when the electrodes are coupled to the tissue. As a result, the device can be easier for the patient and/or clinician to use such that the performance of the device is improved.

In a first aspect, embodiments of the present invention provide a device for monitoring and/or treating a patient, in which the patient has a tissue. The device comprises a battery and circuitry to at least one of monitor or treat the patient. At least two electrodes are configured to couple to the tissue of the patient. At least one switch is coupled to the at least two electrodes, the battery and the circuitry. The at least one switch configured to detect tissue coupling to the at least two electrodes and connect the battery to the circuitry in response to tissue coupling to the at least two electrodes.

In many embodiments, the device comprises start-up circuitry and the start-up circuitry comprises the at least one switch, and the at least one switch closes to connect the battery to the circuitry to at least one of monitor or treat the patient. The circuitry to at least one of monitor or treat the patient and the at least one switch may comprise a low power configuration when the at least one switch is open and a high power configuration when the at least one switch is closed. The start-up circuitry and the circuitry to at least one of monitor or treat the patient can be configured to draw a first amount of current from the battery when the at least one switch is open and a second amount of current when the at least one switch is closed, and the first amount of current may be no more than about one tenth of the second amount of current. The start-up circuitry and the circuitry to at least one of monitor or treat the patient can be configured to draw no more than about 0.5 μA from the battery when the at least one switch is open, and the start-up circuitry and the circuitry to at least one of monitor or treat the patient can be configured to draw at least about 5 μA from the battery when the at least one switch is closed.

In many embodiments, the device comprises a voltage regulator. The at least one switch and the voltage regulator are connected in series between the battery and the circuitry to at least one of monitor or treat the patient, such that the at least one switch and the voltage regulator connect the battery to the circuitry to at least one of monitor or treat the patient.

In many embodiments, the at least one switch comprises an open configuration to disconnect the battery from the circuitry to at least one of monitor or treat the patient. In some embodiments, for example when the at least two electrodes are configured to couple to a skin of the patient, no more than about 0.5 μA of current can pass from the battery when the switch is in the open configuration. In some embodiments, for example when the electrodes are configured to couple to an internal tissue of the patient, no more than about 0.1 μA can pass from the battery when the switch is in the open configuration. In specific embodiments, no more than about 100 pA of current is passed from the battery when the switch is in the open configuration.

In many embodiments, the at least one switch comprises a closed configuration to connect the battery to the circuitry in response to tissue contact with the at least two electrodes. At least about 100 uA of current may pass from the battery when the at least one switch comprises the closed configuration and connects the battery to the circuitry to at least one of monitor or treat the patient, for example when the device is adhered to the skin of the patient.

In many embodiments, the at least one switch comprises a voltage divider and a transistor having a gate with a threshold voltage and wherein the voltage divider and the threshold voltage are configured to close the least one switch when a impedance between the at least two electrodes is below a threshold tissue detection impedance.

In at least some embodiments, the device comprises an implantable device configured to contact the tissue with the at least two electrodes. In some embodiments, one of the at least two electrodes may comprise a housing of the implantable device.

In many embodiments, the tissue comprises skin and the device further comprises at least two gel pads in contact with the at least two electrodes to couple the at least two electrodes to the skin of the patient.

In many embodiments, the at least one switch is configured to connect the battery to the circuitry when the at least one switch detects an impedance between the at least two electrodes below a threshold impedance. The threshold impedance may be within a range from about 2 k-Ohms to about 2 G-Ohm between the at least two electrodes, for example when the electrodes are configured to couple to the skin of the patient. The threshold impedance may comprise a resistance within a range from 2 k-Ohms to 2 G-Ohm. For example, the range can be from about 100 k-Ohms to about 1 G-Ohm. The threshold impedance may comprise at least about 100 Ohms, for example when the at least two electrodes are configured to couple to an internal tissue of the patient.

In many embodiments, the tissue comprises skin having a skin impedance. The device further comprises a removable liner having a liner impedance, and the liner impedance is greater than the skin impedance. The liner impedance may comprise a liner resistance, and the skin impedance may comprise a skin resistance, in which the liner resistance may be greater than the skin resistance. The liner impedance may comprise impedance between the at least two electrodes when the removable liner is positioned over the at least two electrodes. The liner may comprise a substantially waterproof material. The liner may also comprise an impedance sufficient to reduce current flow through the electrodes during storage, for example at least about 10 M-Ohms. This reduction of current flow can be beneficial as the current flow may contribute to degradation of the electrodes and decrease the electrical energy stored in the battery, in at least some instances.

In many embodiments, the liner comprises a cross-sectional thickness and a resistivity and the at least two electrodes comprise a separation distance such that the resistance between the at least two electrodes comprises at least about 10 M-Ohms when the liner is coupled to the at least two electrodes.

In many embodiments, the liner impedance comprises at least about 50 M-Ohms. For example, the liner impedance may comprise a resistance of at least about 50 M-Ohms. The liner resistance may comprise at least about 1 G-Ohm.

In many embodiments, the liner comprises at least one piece. The liner may comprise at least two pieces, in which the at least two pieces comprise a first liner piece and a second liner piece, and the at least two electrodes may comprise a first electrode and a second electrode. The first liner piece can be positioned over the first electrode and the second liner piece can be positioned over the second electrode, such that the first liner piece and the second liner piece at least partially overlap between the first electrode and the second electrode.

In many embodiments, the device further comprises at least two conductive gel pads disposed between the at least two electrodes and the liner. Each of the at least two conductive gel pads may contact one of the at least two electrodes, and the at least two conductive gel pads can be separated to minimize electrical conductance between the at least two electrodes. Each of the at least two conductive gel pads may comprise a solid gel material to separate the at least two conductive gel pads. The liner may protect the at least two conductive gel pads, for example to maintain hydration of the gel pad and also to prevent the device from accidentally turning on during handling.

In many embodiments, the device comprises a support comprising breathable tape affixed to each of the at least two electrodes. The breathable tape comprises an adhesive layer extending between the at least two electrodes, and the liner contacts the adhesive layer and the at least two gel pads. The liner can be configured to separate from the adhesive layer and the at least two gel pads so as to expose the adhesive layer and the at least two gel pads for placement against the skin.

In many embodiments, the support comprising the breathable tape and the adhesive layer comprises an impedance greater than the liner between the at least two electrodes. The impedance of the support between the at least two electrodes and the impedance of the liner between the at least two electrodes are each greater the impedance of the skin when the skin is coupled to the at least two electrodes with the gel pads. For example, the electrical impedance of the support may comprise at least about 10 M-Ohm, for example at least 1 G-Ohm, between the at least two electrodes, and the electrical impedance of the liner may comprise at least about 10 M-Ohm, for example at least 1 G-Ohm, between the at least two electrodes.

In many embodiments, the liner comprises a low stick surface to seal separately each of the at least two conductive gel pads between the support and the liner when the low stick surface of the liner is placed against the adhesive such that conductance between the at least two conductive gel pads is minimized.

In many embodiments, the device further comprises a sealed foil packaging. The sealed foil packaging contains the battery, the circuitry, the at least two electrodes, the at least one switch, the breathable support and the gel pads so as to maintain hydration of the gel pads in storage. The breathable support comprises an impedance of at least about 10 M-Ohms between the at least two electrodes when sealed with the gel pads. This impedance of the breathable support can inhibit false starts of the device, for example when the device is stored in the sealed packaging that can become humid from storage with the gel pads.

In many embodiments, the device further comprises a load coupled to the battery when the at least one switch is open. The load draws no more than about 1 uA of current from the battery when the at least one switch is open.

In many embodiments, the load comprises a clock coupled to the battery when the at least one switch is open, and the clock comprising current date and time information when the at least one switch is open. The circuitry is configured to couple to the clock when the at least one switch is closed to time stamp data measured with the circuitry. This can improve the quality of data because the device can start the patient circuitry with the correct date and time to time stamp that data.

In many embodiments, the circuitry to at least one of monitor or treat the patient comprises the circuitry to monitor the patient. The circuitry to at least one of monitor or treat the patient may comprise the circuitry to treat the patient.

In another aspect, embodiments of the present invention provide a device for monitoring and/or treating a patient, in which the patient has a tissue. The device comprises a battery; and sensor circuitry configured to measure and/or treat the patient. Processor circuitry is coupled to the sensor circuitry and configured to at least one of monitor or treat the patient. At least two electrodes are configured to couple to the tissue of the patient. Start-up circuitry comprises at least one switch coupled to the at least two electrodes, the battery, the sensor circuitry and the processor circuitry. The at least one switch is configured to detect tissue contact with the at least two electrodes and connect the battery to the sensor circuitry and the processor circuitry in response to tissue contact with the at least two electrodes. Sustain circuitry comprises at least one switch to connect the battery to the processor circuitry and the sensor circuitry in response to a signal from the processor.

In many embodiments, the at least one switch of the start-up circuitry and the at least one switch of the sustain circuitry are configured in parallel between the battery and at least one of the sensor circuitry and processor circuitry. The sustain circuitry is capable of sustaining a connection from the battery to the processor circuitry and the sensor circuitry after the tissue is removed from the electrodes and the at least one switch of the start-up circuitry opens. The sustain circuitry may be capable of disconnecting the battery from the processor circuitry and the sensor circuitry after the tissue is removed from the electrodes and the at least one switch of the start-up circuitry opens.

In many embodiments, the processor circuitry is configured to detect disconnection of the tissue from the at least two electrodes. The processor circuitry may be configured to transmit data from the sensor circuitry to a remote center in response to disconnection of the tissue from the at least two electrodes. The processor circuitry can be configured to transmit a signal to a remote center in response to disconnection of the tissue from the electrodes to inform the remote center that tissue has been disconnected from the electrodes.

In another aspect, embodiments of the present invention provide a method of monitoring and/or treating a patient in which that patient has a tissue. A device is provided that comprises circuitry to at least one of monitor or treat the patient. The device comprises a battery and electrodes. The electrodes contact the tissue to deliver power from the battery to the circuitry.

In many embodiments, at least one switch closes to connect the circuitry to the battery when the tissue contacts the electrodes. The at least one switch can open to disconnect the circuitry from the battery when the tissue is removed from the electrodes. The at least one switch may open to disconnect the circuitry from the battery when the tissue is removed from the electrodes. The tissue may be removed from the electrodes. The battery may be disconnected from the circuitry to turn off the circuitry in response to removing the tissue from the circuitry, and a signal may be sent to a remote center in response to removing the tissue from the electrodes.

In another aspect, embodiments of the present invention provide a method of manufacturing a device to at least one of monitor or treat a patient, in which the patient has a tissue. Sensor circuitry, start-up circuitry and electrodes are manufactured. The electrodes are coupled to the start-up circuitry and sensor circuitry. The start-up circuitry comprising at least one switch configured to detect tissue contact with the electrodes. Batteries are installed in the device. The device is shipped with the batteries installed and the device configured such that the start-up circuitry is capable of turning on the device when electrodes of the device contact the tissue of the patient.

In many embodiments, the device comprises a processor and the start-up circuitry is configured to turn on the sensor circuitry and the processor when the electrodes contact the tissue.

In another aspect, embodiments of the present invention provide a method of monitoring a patient. A device is provided that comprises a support, a removable liner, batteries, sensor circuitry, start-up circuitry, at least two electrodes and at least two gel pads in contact with the at least two electrodes. The batteries are coupled to the startup circuitry, and the electrodes are coupled to the start-up circuitry and sensor circuitry. The start-up circuitry comprises at least one switch and is configured to detect tissue coupling to the at least two electrodes. The support comprises an adhesive and is configured to support the batteries, the sensor circuitry, the at least two electrodes and the at least two gel pads with the skin of the patient. The removable liner covers the adhesive and the at least two gel pads. The removable liner is separated from the adhesive and the at least two gel pads to expose the adhesive and the at least two gel pads. The adhesive and the at least two gel pads are placed against the skin of the patient to adhere the device to the patient and couple the electrodes to the skin. The start up circuitry closes the at least one switch to start the sensor circuitry with power from the battery when the at least two gel pads contact the skin of the patient.

BRIEF DESCRIPTION OF THE DRAWINGS

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

FIG. 1E shows batteries positioned over the printed circuit board and electronic components as in FIG. 1D;

FIGS. 1I-1 and 1J-1 show the adherent device as in FIGS. 1A to 1J with a removable liner positioned over the gel;

FIG. 1J-2 shows a removable liner comprising a first piece and a second piece with overlap between the first piece and the second piece;

FIG. 2B-1 shows the start-up circuitry of FIG. 2B with a removable liner coupled to the electrodes;

DETAILED DESCRIPTION OF THE INVENTION

Embodiments of the present invention relate to patient monitoring. Although embodiments make specific reference to monitoring impedance and electrocardiogram signals with an adherent patch, the system methods and device described herein may be applicable to many application in which physiological monitoring is used, for example physiological monitoring with implantable devices.

Work in relation to embodiments of the present invention indicates that start-up circuitry with low power consumption can make a patient monitoring and/or treatment device easier to use and may extend the useful life of the electrodes of the device. It can be helpful if current flow through the electrodes from the start-up circuitry can be minimized. This minimization of the current flow can have many benefits including increased storage life of the device, increased battery life, and also minimized damage and/or wear to the electrodes and so as to maximize the useful life of the electrodes. As the start-up circuitry has very low power consumption, for example less than about 100 pA, the start-up circuitry can remain connected to the battery or other power supply for extended periods of time, for example at least six months. The device may comprise a protective liner to cover at least one of the electrodes or a gel positioned over the electrodes, such that the integrity of the electrodes and gel are maintained during storage and handling. For example, the liner can maintain hydration of the gel. Therefore, the device can be shipped to the patient and/or clinician with the batteries installed such that the device is capable of turning on automatically when electrodes of the device are coupled to tissue, for example placed against patient tissue such as skin. The start-up circuitry is compact and can be used with external devices, for example adherent devices, and implantable devices, for example injectable devices.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the patch can be worn and/or tolerated by the patient for extended periods, for example 90 days or more. In many embodiments, the adherent patch comprises a tape, which comprises a material, preferably breathable, with an adhesive, such that trauma to the patient skin can be minimized while the patch is worn for the extended period. In many embodiments, the printed circuit board comprises a flex printed circuit board that can flex with the patient to provide improved patient comfort.

Figure 1A:
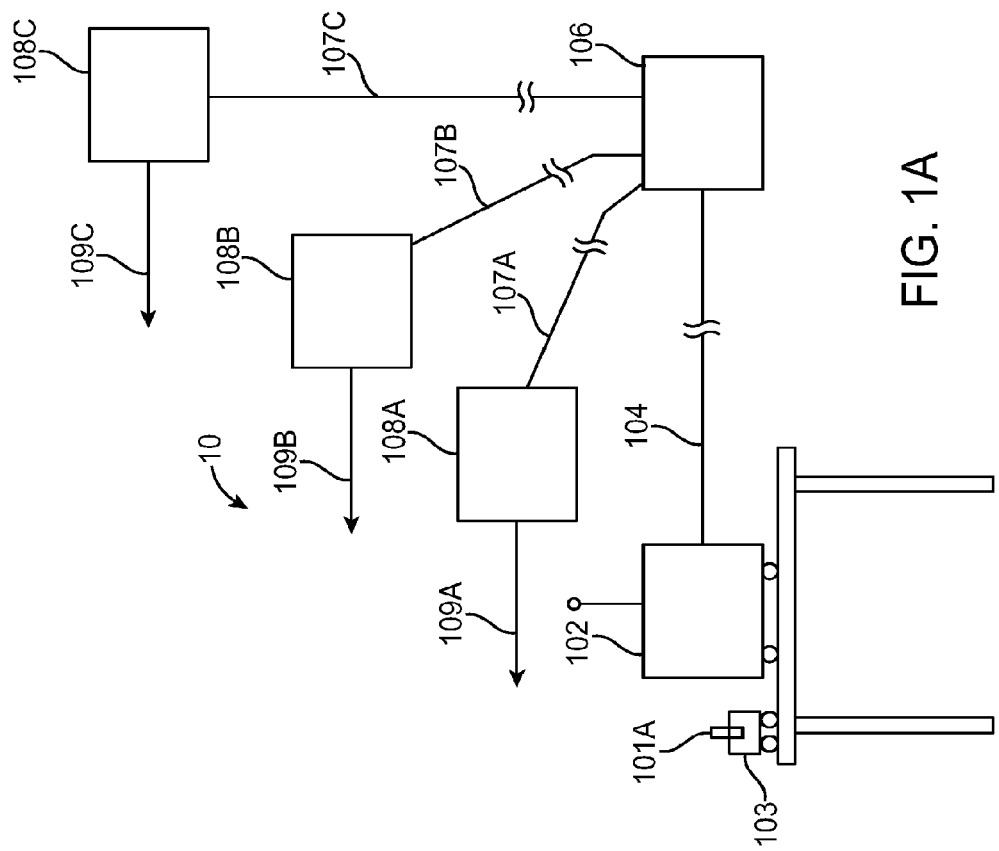
FIG. 1A shows a patient and a monitoring system comprising an adherent device, according to embodiments of the present invention.
Figure 1A:
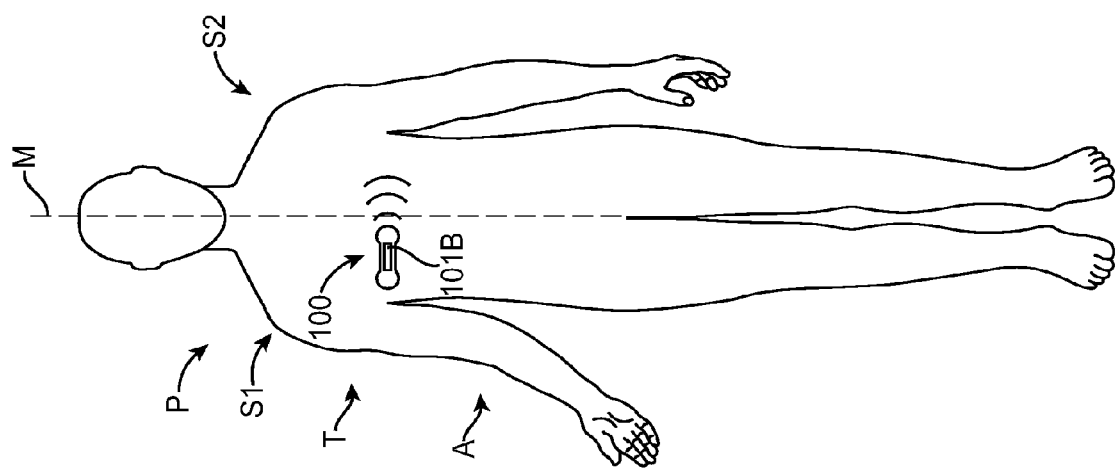

FIG. 1A shows a patient P and a monitoring system 10. Patient P comprises a midline M, a first side S1, for example a right side, and a second side S2, for example a left side. Monitoring system 10 comprises a patient device, for example an adherent device 100. In some embodiments, the patient device may comprise an implantable device such as a cardiac pacemaker. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Adherent device 100 comprises low power start-up circuitry connected to the battery to detect when the device is adhered to the patient and turn on the patient monitoring circuitry. The low power start up circuitry may comprise at least one switch configured to detect tissue. The low power start-up circuitry and the circuitry to at least one of monitor or treat the patient can be configured to draw a first amount of current from the battery when the at least one switch is open and a second amount of current when the at least one switch is closed. The device may comprise a low power configuration when the at least one switch is open and a high power configuration when the at least one switch is closed. The first amount of current may be no more than about one tenth of the second amount of current. For example, the start-up circuitry and the circuitry to at least one of monitor or treat the patient may be configured to draw no more than about 0.5 µA from the battery when the at least one switch is open, and the start-up circuitry and the circuitry to at least one of monitor or treat the patient may be configured to draw at least about 5 µA from the battery when the at least one switch is closed, for example at least about 10 µA. Therefore the device may comprise a low power configuration, or mode, with a total current consumption of no more than about 0.5 µA from the battery and a high power configuration, or mode, with a total current consumption from the battery of at least about 5 µA. With the embodiments described herein, much lower current can be used to run the device in the low power mode. For example, no more than about 0.1 µA of current may pass from the battery when the switch is in the open configuration, and the current passed from the battery with the switch in the open configuration may be no more than about 100 pA, or less. In the low power configuration, the current consumption from the battery of adherent device with the at least one switch open can be any amount from about 100 pA to 0.5 µA, for example 1 nA, 10 nA or 100 nA. With implantable devices, for example injectable devices, the amount of current consumed from the battery in the lower power configuration and the high power configuration can each be substantially lower than for an adherent device, for example at least an order of magnitude lower, for example about two orders of magnitude lower.

Monitoring system 10 includes components to transmit data to a remote center 106. Adherent device 100 can communicate wirelessly to an intermediate device 102, for example with a single wireless hop from the adherent device on the patient to the intermediate device. Intermediate device 102 can communicate with remote center 106 in many ways, for example with an internet connection. In many embodiments, monitoring system 10 comprises a distributed processing system with at least one processor on device 100, at least one processor on intermediate device 102, and at least one processor at remote center 106, each of which processors is in electronic communication with the other processors. Remote center 106 can be in communication with a health care provider 108A with a communication system 107A, such as the Internet, an intranet, phone lines, wireless and/or satellite phone. Health care provider 108A, for example a family member, can be in communication with patient P, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In the many embodiments, the remote center receives the data and applies a data analysis algorithm. When a flag is raised, the center may communicate with the patient, hospital, nurse, and/or physician to allow for therapeutic intervention.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive model for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches. For example, each patch may last an extended period of at least one week, for example at least two weeks, and the patch can be replaced with a subsequent patch. The reusable module can collect cumulative data for approximately 90 days.

In at least some embodiments, the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent device. In some embodiments, the intermediate device 102 may comprise the charging module, data transfer, storage and/or transmission, such that one of the electronics modules can be placed in the intermediate device for charging and/or data transfer while the other electronics module is worn by the patient.

In many embodiments, the system can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, HRV, HRT, heart sounds (e.g. S3), respiratory sounds, blood pressure, activity, posture, wake/sleep, orthopnea, temperature/heat flux, and weight. The activity sensor may be one of the following: ball switch, accelerometer, minute ventilation, HR, bioimpedance noise, skin temperature/heat flux, BP, muscle noise, posture.

In many embodiments, the patch wirelessly communicates with a remote center. In some embodiments, the communication may occur directly (via a cellular or Wi-Fi network), or indirectly through intermediate device 102. Intermediate device 102 may consist of multiple devices which communicate wired or wirelessly to relay data to remote center 106.

In many embodiments, instructions are transmitted from a remote site to a processor supported with the patient, and the processor supported with the patient can receive updated instructions for the patient treatment and/or monitoring, for example while worn by the patient.

Figure 1B:
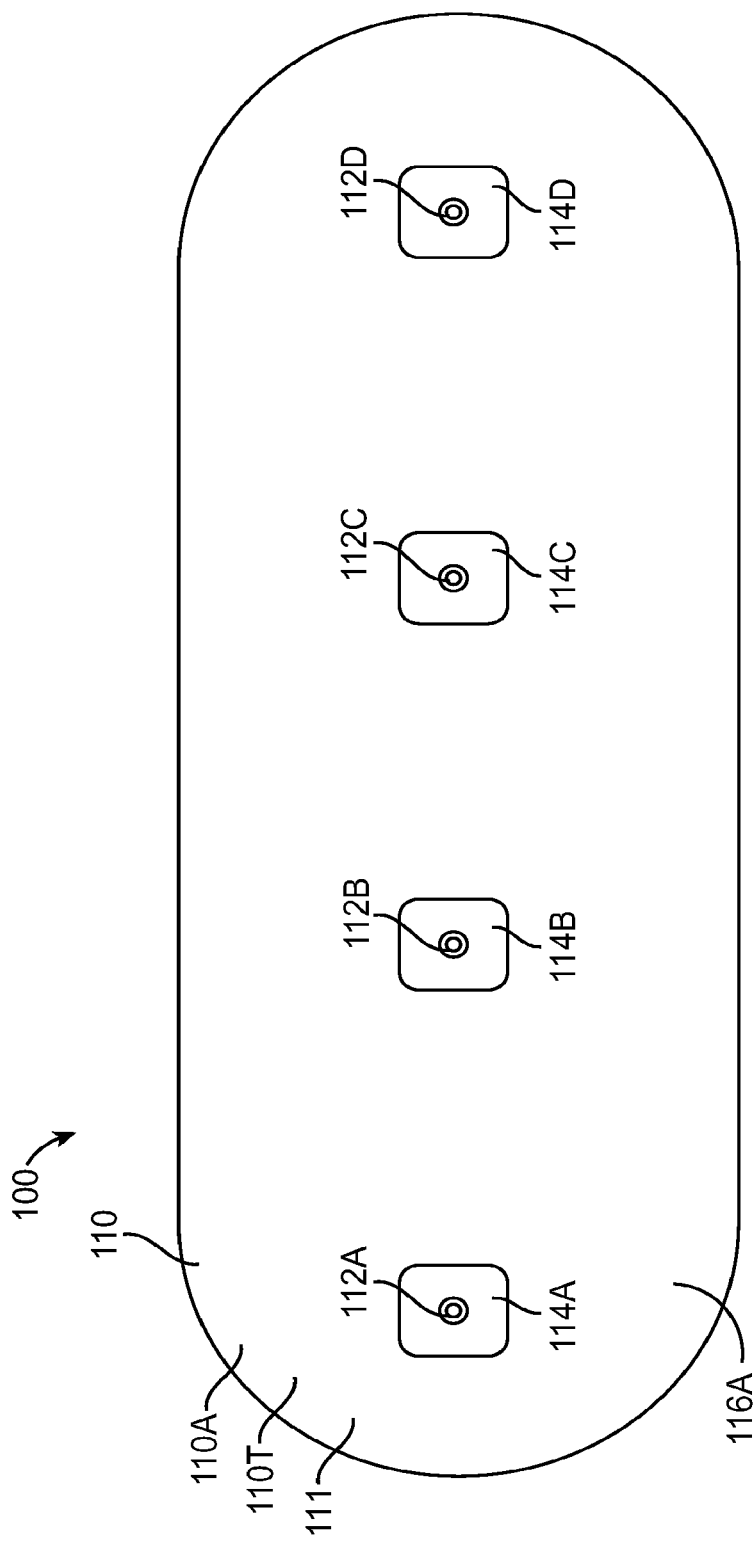
FIG. 1B shows a bottom view of the adherent device as in FIG. 1A comprising an adherent patch.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each comprise a gel pad positioned over electrodes 112A, 112B, 112C and 112D, respectively, to provide electrical conductivity between the electrodes and the skin of the patient. The gel pads may each comprise a solid gel material, for example a solid hydrogel, that retains the size and shape of the gel pad when positioned over the electrode, such that each gel pad on each electrode remains separated from the other gel pads on the other electrodes. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
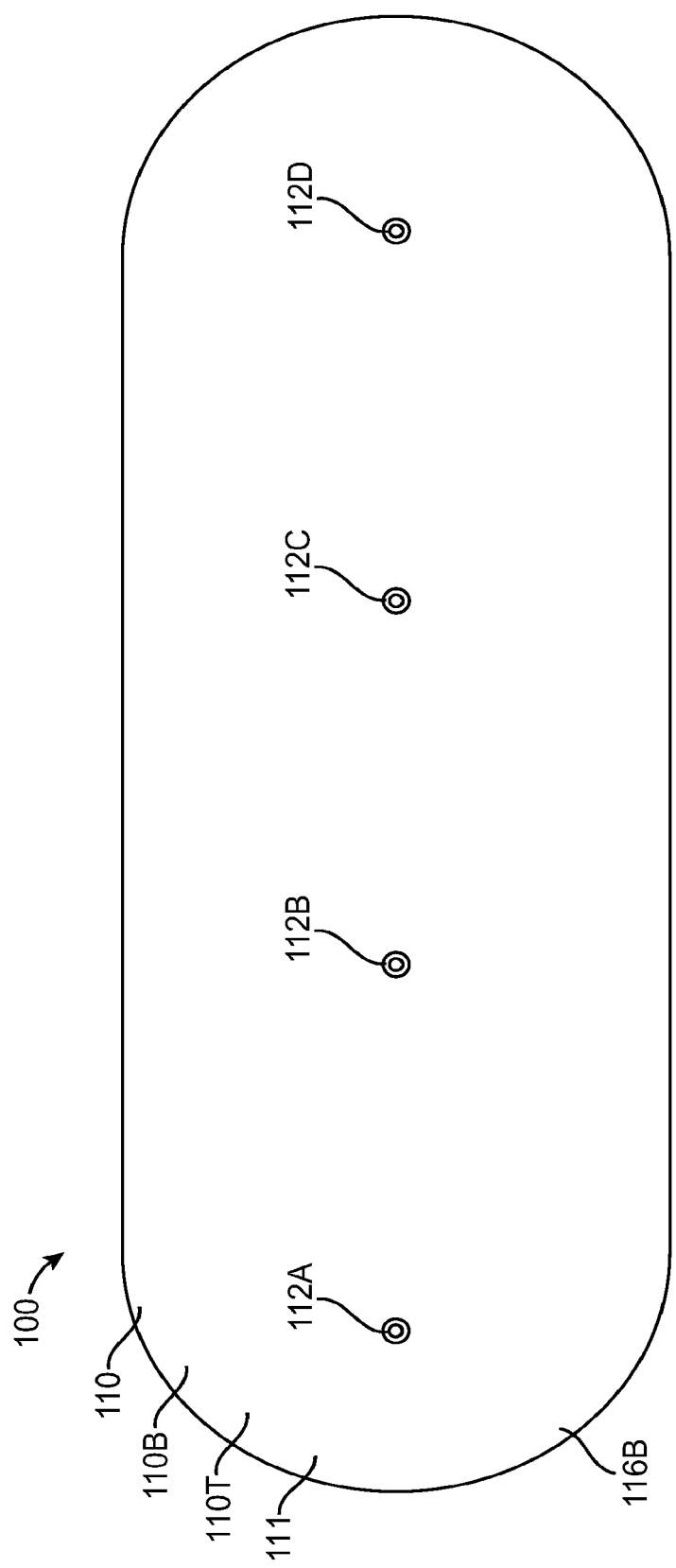
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 110A, 110B, 110C and 110D extend from lower side 110A through the adherent patch to upper side 110B. In some embodiments, an adhesive 116B can be applied to upper side 110B to adhere structures, for example electronic structures, to the patch such that the patch can support the electronics and other structures when the patch is adhered to the patient. The PCB comprise completely flex PCB, rigid PCB combined flex PCB and/or rigid PCB boards connected by cable.

FIG. 1D shows a printed circuit boards and electronic components over adherent patch 110, as in FIG. 1C. In some embodiments, a printed circuit board (PCB), for example flex PCB 120, may be connected to upper side 100B of patch 110 with connectors 122A, 122B, 122C and 122D. Flex PCB 120 can include traces 123A, 123B, 123C and 123D that extend to connectors 122A, 122B, 122C and 122D, respectively, on the flex PCB. Connectors 122A, 122B, 122C and 122D can be positioned on flex PCB 120 in alignment with electrodes 112A, 112B, 112C and 112D so as to electrically couple the flex PCB with the electrodes. In some embodiments, connectors 122A, 122B, 122C and 122D may comprise insulated wires that provide strain relief between the PCB and the electrodes. In some embodiments, additional PCB's, for example rigid PCB's 120A, 120B, 120C and 120D, can be connected to flex PCB 120. Electronic components 130 can be connected to flex PCB 120 and/or mounted thereon. In some embodiments, electronic components 130 can be mounted on the additional PCB's.

The electronic components of device 100 comprise start-up circuitry 142 and electronic components 130 to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 may comprise accelerometer circuitry 134, impedance circuitry 136 and electrocardiogram circuitry, for example ECG circuitry 136. Electronics circuitry 130 may comprise a temperature sensor, for example a thermistor, and temperature sensor circuitry 144 to measure a temperature of the patient, for example a temperature of a skin of the patient.

Start-up circuitry 142 can control power to the electronic components 130, such that electronics components 130 use very little power when the adherent device is not connected to the patient. Start-up circuitry 142 may comprise at least one switch connected in series between a power source, for example a battery, and electronic components 130, such that the electronics components can be disconnected from the power source when the at least one switch of start-up circuitry 130 comprises an open configuration. When the electrodes contact tissue, start-up circuitry 142 closes the at least one switch to connect electronic components 130 with the power source, for example the battery.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication methodology may comprise many known communication methodologies, for example at least one of Bluetooth, Zigbee, WiFi or WiMax. The communication signal may comprise many known communication signals, such as IR, amplitude modulation or frequency modulation. In many embodiments, the communications protocol comprises a two way protocol, and the two way protocol can be configured such that the remote center is capable of issuing commands to control data collection.

In some embodiments, intermediate device 102 comprises a data collection system to collect and store data from the wireless transmitter. The data collection system can be configured to communicate periodically with the remote center. In many embodiments, the data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data. In some embodiments, an accelerometer with one or two axes can also provide useful patient information.

Impedance circuitry 136 can generate both hydration data and respiration data. In many embodiments, impedance circuitry 136 is electrically connected to electrodes 112A, 112B, 112C and 112D such that electrodes 112A and 112D comprise outer electrodes that are driven with a current, or force electrodes. The current delivered between electrodes 112A and 112D generates a measurable voltage between electrodes 112B and 112C, such that electrodes 112B and 112C comprise inner electrodes, or sense electrodes that measure the voltage in response to the current from the force electrodes. The voltage measured by the sense electrodes can be used to determine the hydration of the patient.

Figure 1F:
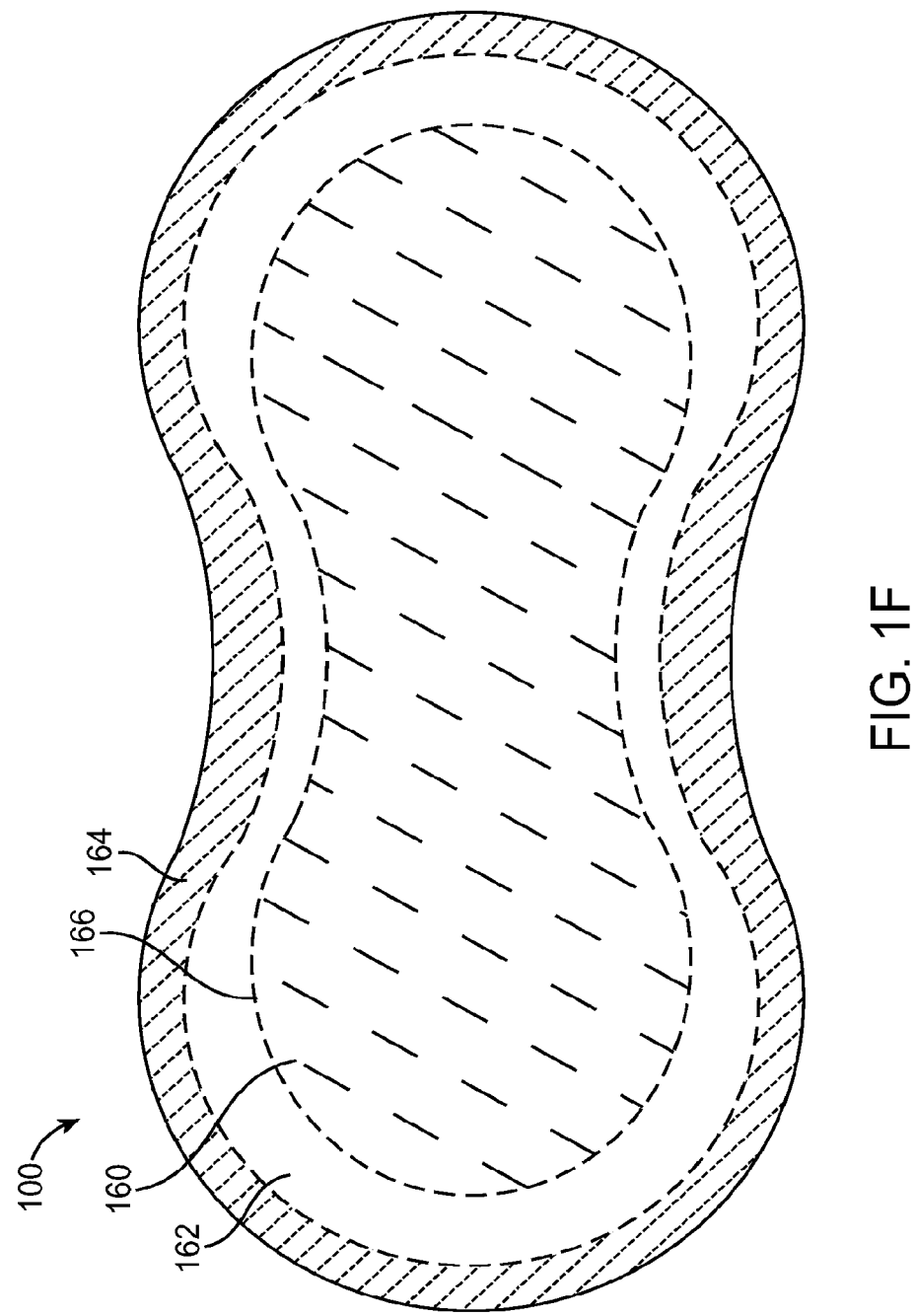
FIG. 1F shows a top view of an electronics housing and a breathable cover over the batteries, electronic components and printed circuit board as in FIG. 1E.
Figure 1G:
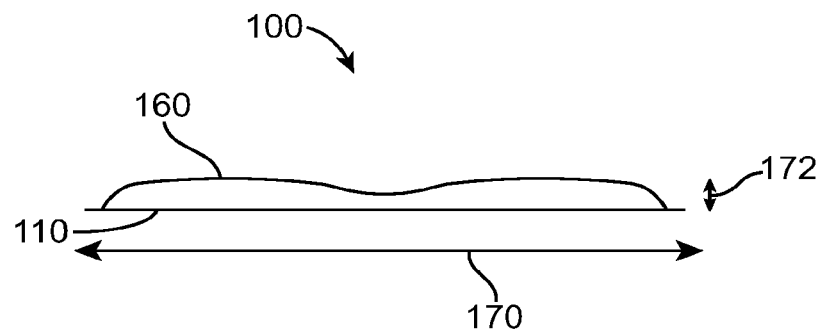
FIG. 1G shows a side view of the adherent device as in FIGS. 1A to 1F.
Figure 1H:
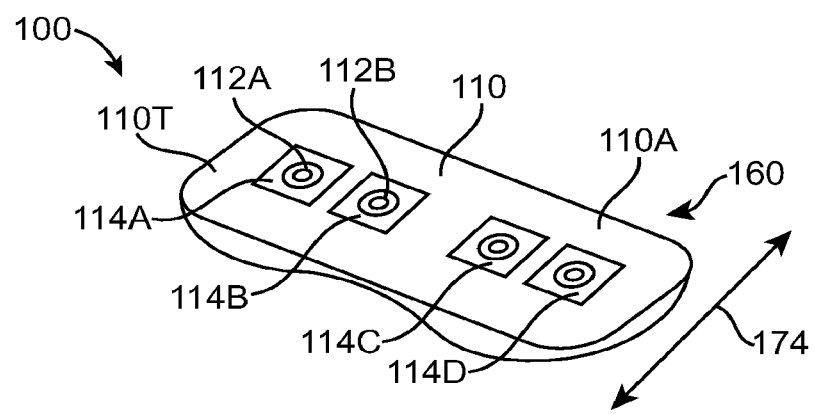
FIG. 1H shown a bottom isometric view of the adherent device as in FIGS. 1A to 1G.
Figure 1I:
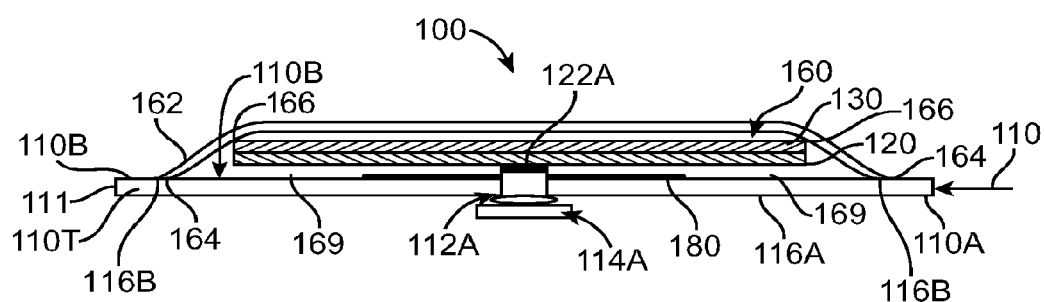
FIGS. 1I and 1J show a side cross-sectional view and an exploded view, respectively, of the adherent device as in FIGS. 1A to 1H.
Figures 1, 1I:
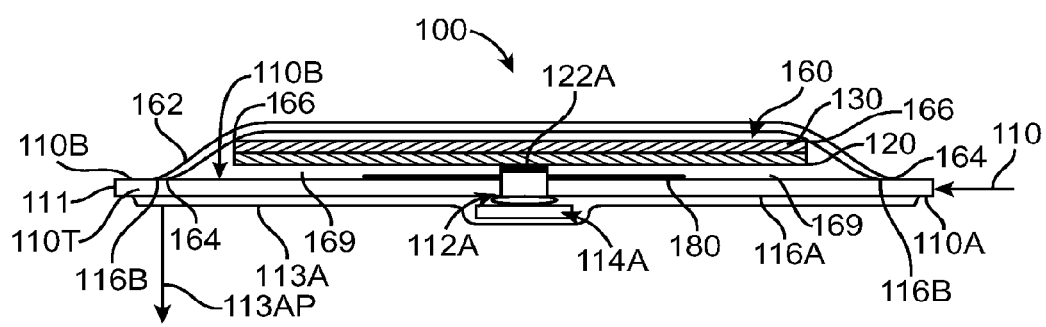

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention employ measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from electrodes 112A, 112B, 112C and 112D. In some embodiments, ECG circuitry 138 is connected to inner electrodes 112B and 122C, which may comprise sense electrodes of the impedance circuitry as described above. In some embodiments, the inner electrodes may be positioned near the outer electrodes to increase the voltage of the ECG signal measured by ECG circuitry 138. In some embodiments, the ECG circuitry can share components with the impedance circuitry.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

FIG. 1F shows a top view of a cover 162 over the batteries, electronic components and flex printed circuit board as in FIG. 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adhesive patch with an adhesive 164 on an underside of cover 162. In some embodiments, electronics housing 160 can be adhered to cover 162 with an adhesive 166 where cover 162 contacts electronics housing 160. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1J:
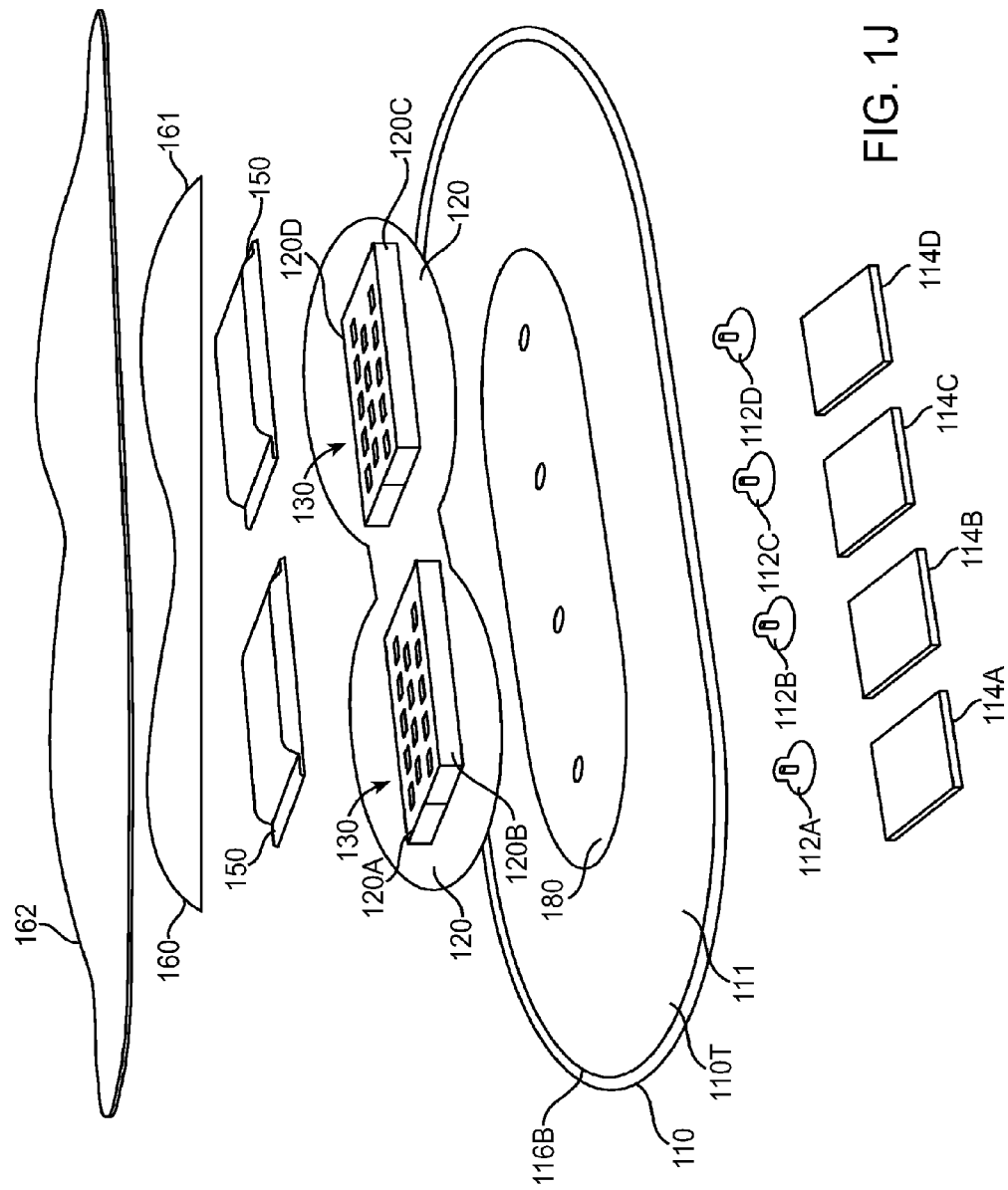
Figures 1, 1J:
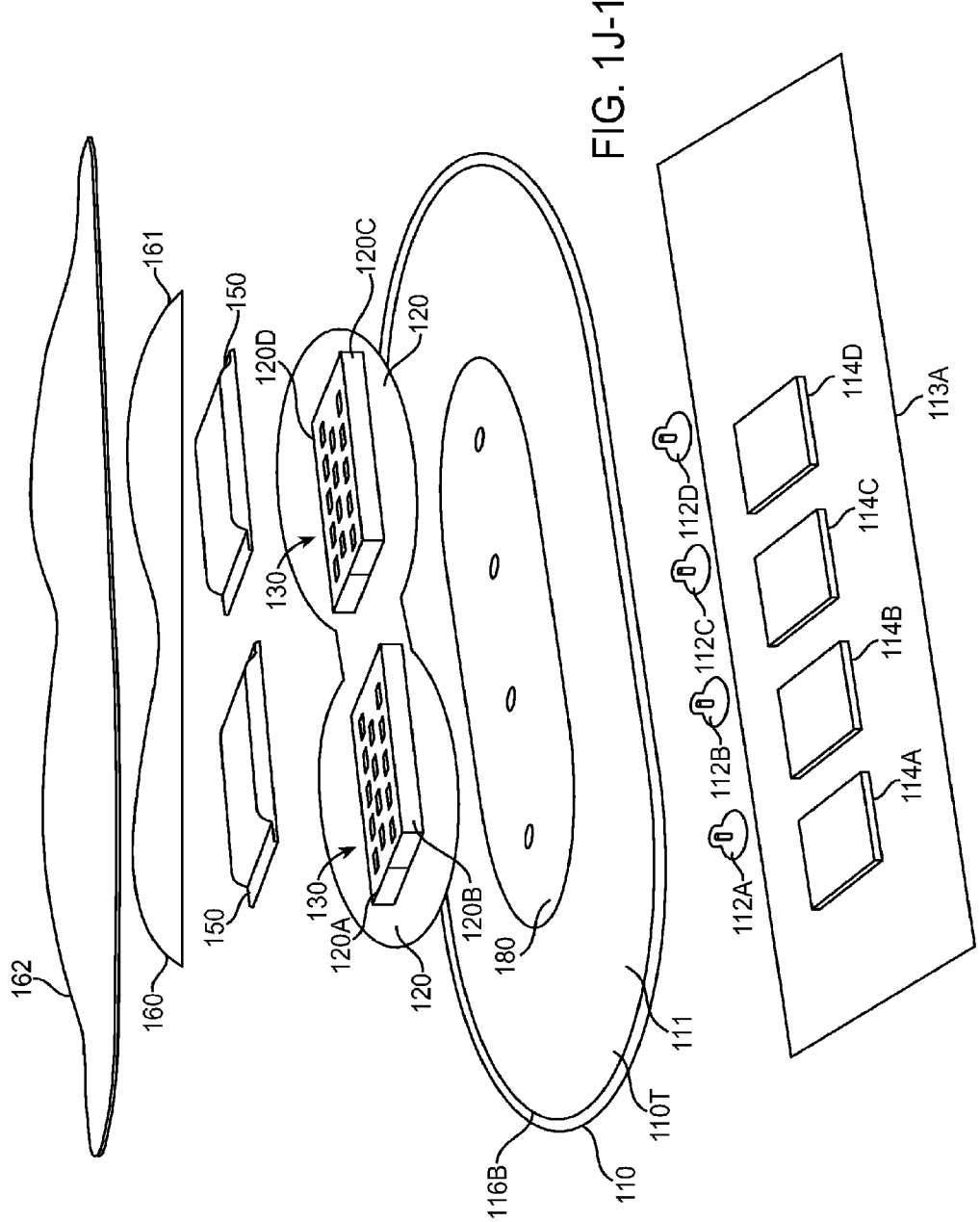

FIGS. 1I and 1J show a side cross-sectional view and an exploded view, respectively, of adherent device 100 as in FIGS. 1A to 1H. Device 100 comprises several layers. Gel 114A, or gel layer, may comprise a gel pad and is positioned on electrode 112A to provide electrical conductivity between the electrode and the skin. Electrode 112A may comprise an electrode layer. Adhesive patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of patch 110. A gel cover 180, or gel cover layer, for example a polyurethane non-woven tape, can be positioned over patch 110 comprising the breathable tape. A PCB layer, for example flex PCB 120, or flex PCB layer, can be positioned over gel cover 180 with electronic components 130 connected and/or mounted to flex PCB 120, for example mounted on flex PCB so as to comprise an electronics layer disposed on the flex PCB. In many embodiments, the adherent device may comprise a segmented inner component, for example the PCB, for limited flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex PCB 120, so as to provide strain relive between the electrodes 112A, 112B, 112C and 112D and the PCB. Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture from penetrating into gel 114A. In many embodiments, cover 162 can encase the flex PCB and/or electronics and can be adhered to at least one of the electronics, the flex PCB or the adherent patch, so as to protect the device. In some embodiments, cover 162 attaches to adhesive patch 110 with adhesive 116B, and cover 162 is adhered to the PCB module with an adhesive 161 on the upper surface of the electronics housing. Cover 162 can comprise many known biocompatible cover, housing and/or casing materials, for example silicone. In many embodiments, cover 162 comprises an outer polymer cover to provide smooth contour without limiting flexibility. In some embodiments, cover 162 may comprise a breathable fabric. Cover 162 may comprise many known breathable fabrics, for example breathable fabrics as described above. In some embodiments, the breathable fabric may comprise polyester, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

FIGS. 1I-1 and 1J-1 show the adherent device as in FIGS. 1A to 1J with a removable liner 113A positioned over the gel 114A, gel 114B, gel 114C and gel 114D, or gel pads. Removable liner 113A can cover the underside of the adhesive patch 110, the at least two electrodes and the gel pads, for example at least two gel pads comprising gel 114A and gel 114D. Liner 113A may comprise a material having an impedance, for example a resistance, greater than human skin. The liner 113A prevents the at least two electrodes from detecting an impedance or resistance similar to human tissue and activating the start-up circuitry, for example when the device is stored with the batteries positioned in the device for use prior to placement on the patient. The electrical impedance of the liner 113A as measured from the electrodes can be greater than 50 M-Ohms, and may comprise a resistance greater than 50 M-Ohms, for example a resistance greater than about 1 G-Ohms. The threshold electrical resistance between the at least two electrodes that activates the start-up circuit can be within a range from about 2 k-Ohms to about 2 G-Ohms, for example from about 100 k-Ohms to about 1 G-Ohms. The liner 113A may also cover the adhesive coating 116A on the underside of the adhesive patch 110 so as to keep the adhesive coating 116A clean so that the adhesive will adhere to the patient's skin when the gel pads and adhesive are placed against the skin of the patient. The liner 113A comprises a non-stick surface in contact with the adhesive such that the liner can be peeled away from the adhesive on the underside of the adhesive patch 110, as indicated by arrow 113AP, so that the adhesive and gel pads can be applied to the skin of the patient.

Figures 1, 1J, 2:
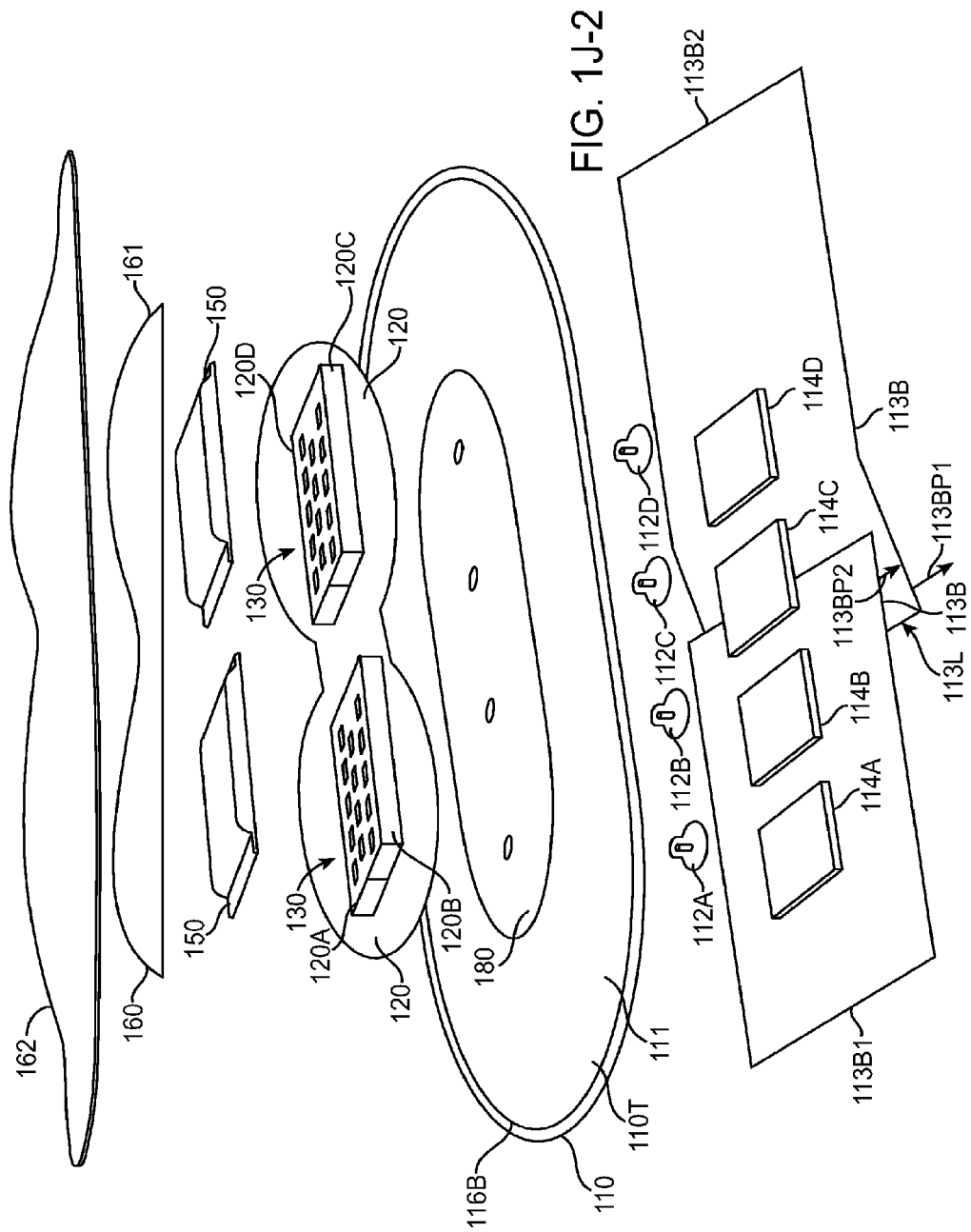

FIG. 1J-2 shows a liner 113B, similar to liner 113A, and comprising a first piece 113B1 and a second piece 113B2 with overlap between the first piece and the second piece. First piece 113B1 and second piece 113B2 may be sized and positioned so as to provide an overlap 113L between the first piece and the second piece. Overlap 113L can facilitates separation of the first and second pieces of the liner from the adhesive. First liner piece 113B1 can be pulled from second liner piece 113B2 at overlap 113L, as indicated by arrow 113BP1. Second liner piece 113B2 can be pulled from adhesive 116A as indicated by arrow 113BP2.

In many embodiments, the breathable tape of adhesive patch 110 comprises a first mesh with a first porosity and gel cover 180 comprises a breathable tape with a second mesh porosity, in which the second porosity is less than the first porosity to inhibit flow of the gel through the breathable tape.

In many embodiments, a gap 169 extends from adherent patch 110 to the electronics module and/or PCB, such that breathable tape 110T can breath to provide patient comfort.

In many embodiments, the adherent device comprises a patch component and at least one electronics module. The patch component may comprise adhesive patch 110 comprising the breathable tape with adhesive coating 116A, at least one electrode 114A and gel 114, for example a gel coating. The at least one electronics module can be is separable from the patch component. In many embodiments, the at least one electronics module comprises the flex printed circuit board 120, electronic component 130, electronics housing 160 and waterproof cover 162, such that the flex printed circuit board, electronic components electronics housing and water proof cover are reusable and/or removable for recharging and data transfer, for example as described above. In many embodiments, adhesive 116B is coated on upper side 110A of adhesive patch 110B, such that the electronics module, or electronics layers, can be adhered to and/or separated from the adhesive component, or adhesive layers. In specific embodiments, the electronic module can be adhered to the patch component with a releasable connection, for example with Velcro™, a known hook and loop connection, and/or snap directly to the electrodes. In some embodiments, two electronics modules can be provided, such that one electronics module can be worn by the patient while the other is charged as described above.

In many embodiments, at least one electrode 112A extends through at least one aperture in the breathable tape 110.

In some embodiments, the adhesive patch may comprise a medicated patch that releases a medicament, such as antibiotic, beta-blocker, ACE inhibitor, diuretic, or steroid to reduce skin irritation. In some embodiments, the adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

Figure 2A:
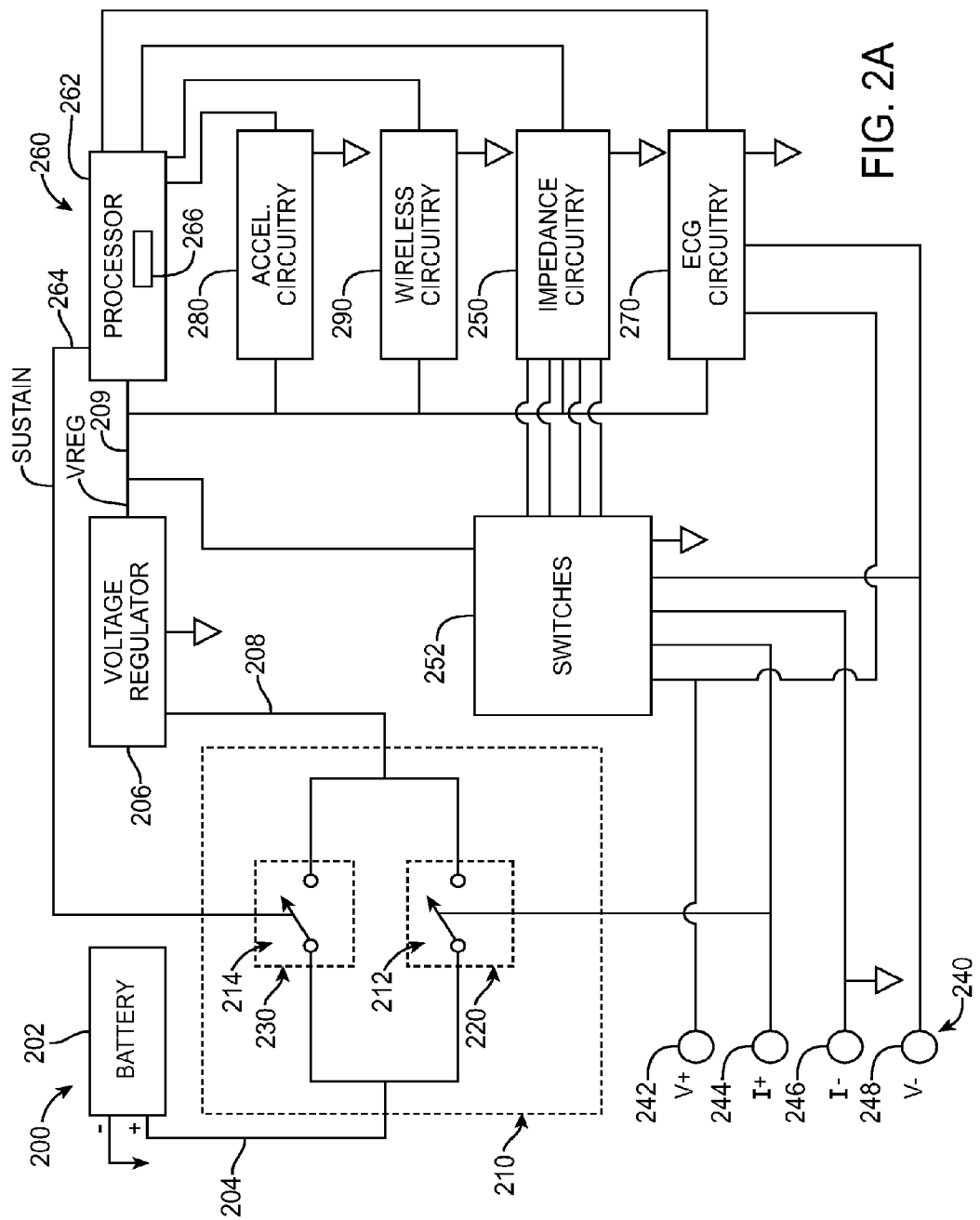
FIG. 2A shows a simplified schematic illustration of a circuit for automatically turning on the device when tissue contacts with the electrodes, and in which the processor is able to turn off the device after tissue is removed from the electrodes, according to embodiments of the present invention.

FIG. 2A shows a simplified schematic illustration of a circuitry 200 for automatically turning on the device when tissue contacts the electrodes, and in which the processor is able to turn off the device after tissue is removed from the electrodes. Circuitry 200 can be used with many kinds of patient devices, for example an adherent device as described above, an implantable device such as a pacemaker. Circuitry 200 can also be adapted for use with injectable devices. Circuit 200 comprises a least four electrodes 240. At least four electrodes 240 comprise a V+ electrode 242, an I+ electrode 244, an I− electrode 246 and a V− electrode 248. At least four electrodes 240 can be used to measure signals from tissue, for example bioimpedance signals and ECG signals. Although at least four electrodes 240 are shown, in some embodiments the circuit can detect tissue contact with two electrodes, for example I+ electrode 244 and I− electrode 244.

Circuit 200 comprises a battery 202 for power. Battery 202 may comprise at least one of a rechargeable battery or a disposable battery, and battery 202 may be connected to an inductive coil to charge the battery. Battery 202 comprises an output 204.

Circuit 200 comprises a voltage regulator 206. Voltage regulator 206 may comprise a known voltage regulator to provide a regulated voltage to the components of circuit 200. Voltage regulator 206 comprises an input that can be connected to battery output 204 to provide regulated voltage to the components of circuit 200.

Circuitry 200 comprises power management circuitry 210. Power management circuitry 210 can be connected in series between battery output 204 and voltage regulator 206, and can start-up and turn off components of circuitry 200. Power management circuitry 210 comprises a start-up circuitry 220 and sustain circuitry 230. Start-up circuitry 220 comprises at least one switch 212 and sustain circuitry 230 comprises at least one switch 214. At least one switch 212 of start-up circuitry 220 and at least one switch 214 of sustain circuitry 230 are in a parallel configuration, such that either switch is capable of connecting battery 202 to voltage regulator 206. Power management circuitry 210 can start-up and turn off components of circuitry 200 with at least one switch 212 of start-up circuitry 220 and at least one switch 214 of sustain circuitry 230. At least one switch 212 can detect tissue contact to the electrodes and close to connect the battery to the circuitry and start-up components of circuitry 200. At least one switch 212 can open and may disconnect voltage regulator 206 from battery output 204 when tissue disconnects from the electrodes. Components of circuitry 200 that can be turned on and off with output 209 of voltage regulator 206 include impedance circuitry 250, switches 252, a processor 262, ECG circuitry 270, accelerometer circuitry 280, and wireless circuitry 290. Circuitry 200 may comprise a processor system 260, for example with distributed processors, such that processor 262 of processing system 260 can be turned on and off with output 209 from at least one switch 212, at least one switch 214 and/or voltage regulator 206.

Start-up circuitry 220 can detect tissue contact with electrodes and close at least one switch 212, for example a transistor, between battery output 204 and voltage regulator 206, so as to control power regulator 206. Prior to tissue contacting the electrodes, at least one switch 212 of start-up circuitry 220 comprises an open configuration, such that no power flows from battery 202 to regulator 206. When at least one switch 212 and at least one switch 214 are open, very little current flows from battery 202. Work in relation to embodiments of the present invention indicates that current from battery 202 may be no more than about 100 pA ($100*10^{-12}$ A), for example about 35 pA, such that the life of battery 202 is determined primarily by the storage life of the battery with no significant effect from start-up circuitry 202. When tissue contacts the electrodes, for example I+ electrode 244 and I− electrode 246, at least one switch 212 of start-up circuitry 220 closes and battery 202 is connected to voltage regulator 206, such that power is delivered to the components of circuitry 202 that depend on regulated voltage from regulator 206 for power. Thus, start-up circuitry 220 can start components of circuitry 200, for example those components that depend on regulated voltage and power regulator 206 as described above.

Although voltage regulator 206 is shown, the voltage regulator may not be present in some embodiments, such that at least one switch 212 can connect battery 202 to at least some components of circuitry 200 without a voltage regulator. For example at least one of impedance circuitry 250, switches 252, a processor 262, ECG circuitry 270, accelerometer circuitry 280, or wireless circuitry 290 may be powered without the voltage regulator when at least one switch 212 closes to connect battery 202 with these components.

Sustain circuitry 230 can sustain power to the regulator after tissue is removed from the electrodes. Sustain circuitry 230 allows battery 202 to remain connected to the power supply 206 and the associated circuitry, even after tissue is removed from the electrodes and at least one switch 212 opens, such that the connection between battery 202 and voltage regulator 206 can be sustained with at least one switch 214. At least one switch 214 of sustain circuitry 230 can connect battery 202 to regulator 206 when at least one switch 214 is closed and disconnect battery 202 from regulator 206 when at least one switch 214 is open. Processor 262 can be coupled to sustain circuitry 230 with a control line 264. When the start-up circuitry 220 powers up the regulator and processor 262, processor 262 asserts a digital on signal voltage on control line 264 so as to close at least one switch 214. Thereafter, processor 262 can continue to assert control line 264 with a digital on signal voltage such that sustain circuitry 230 remains closed, even after tissue is removed from the electrodes. When processor 262 asserts an off signal voltage on control line 264, sustain circuitry 230 opens at least one switch 214 between battery output 204 and voltage regulator 206 and may turn off the components connected to voltage regulator 206, including the processor.

Sustain circuitry 230 can be configured to shut down power to the voltage regulator and associated circuitry components after tissue is removed from contact with the electrodes. As noted above at least one switch 212 can open when tissue is disconnected from the electrodes. When at least one switch 212 is open, for example after the electrodes are disconnected from tissue, processor 262 can assert a digital off voltage signal on control line 264 so as to open at least one switch 214 such that processor 262 shuts itself down with a shutdown process.

Processor 262 can be configured to detect opening of at least one switch 212 in response to disconnection of tissue from the electrodes, such that the processor can respond to the disconnection of tissue in a controlled matter before the processor is shut down. In response to opening at least one switch 212, processor 262 may initiate processes, such as wireless transmission of data of data stored on processor 262 prior to the shutdown process. Processor 262 may also transmit a signal to a remote center, as described above, indicating that the patch has been removed from the patient. Once these processes are completed, processor 262 can execute the shutdown process by delivering an off signal voltage on control line 264 such that at least one switch 214 opens and processor 262 is turned off.

In specific embodiments, sustain circuitry 230 may comprise an additional switch that is in series with start-up circuitry 220 such that the additional switch can open to disconnect power from battery 202 to voltage regulator 206 while tissue remains in contact with the electrodes.

Circuitry 200 may comprise an accelerometer 280 to measure patient orientation, acceleration and/or activity of the patient. Accelerometer 280 may comprise many known accelerometers, for example three dimensional accelerometers. Accelerometer 280 may be connected to processor 262 to process signals from accelerometer 280.

Circuitry 200 may comprise wireless circuitry 290. Wireless circuitry 290 may comprise known wireless circuitry for wireless communication from the device. Wireless communications circuitry 290 can communicate with remote center as described above. The wireless communication circuitry can be coupled to the impedance circuitry, the electrocardiogram circuitry and the accelerometer to transmit to a remote center with a communication protocol at least one of the hydration signal, the electrocardiogram signal or the inclination signal from the accelerometer. In specific embodiments, wireless communication circuitry is configured to transmit the hydration signal, the electrocardiogram signal and the inclination signal to the remote center with a single wireless hop, for example from wireless communication circuitry 290 to the intermediate device as described above. As noted above, the communication methodology may comprise at least one of Bluetooth, Zigbee, WiFi, WiMax, and the communication signal may comprise IR, amplitude modulation or frequency modulation. In many embodiments, the communications protocol comprises a two way protocol configured such that the remote center is capable of issuing commands to control data collection.

Processor system 260 may comprise processors in addition to processor 262, for example a remote processor as described above. Processor 262 comprises tangible medium 266 that can be configured with instructions, and tangible medium 266 may comprise memory such as random access memory (RAM), read only memory (ROM), erasable read only memory (EPROM), and many additional types of known computer memory. Processor system 260 comprising processor 262 can be connected to impedance circuitry 250, switches 252, a processor 262, ECG circuitry 270, accelerometer circuitry 280, and wireless circuitry 290 to transmit and/or process data.

Circuitry 200 comprises impedance circuitry 250 for measuring tissue impedance. Impedance circuitry 250 may comprise switches 252 to connect the impedance circuitry to at least four electrodes 240. In specific embodiments, V+ electrode 242 and V− electrode 248 are connected to drive circuitry of impedance circuitry 250 to drive a current through the tissue. An impedance signal comprising voltage drop can occur along the tissue as a result of the drive current, and I+ electrode 244 and I− electrode 246 can be connected to measurement circuitry of impedance circuitry 250 to measure the impedance signal from the tissue. Processor 262 can be coupled to switches 252 to connect at least four electrodes 240 to impedance circuitry 240.

Figure 2B:
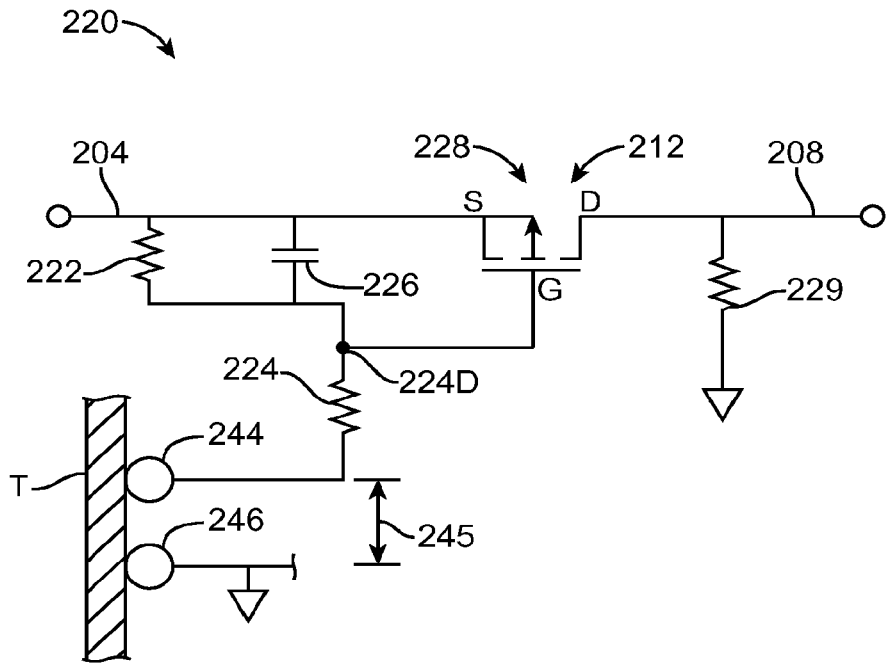
FIG. 2B shows additional detail of start-up circuitry of FIG. 2A that automatically turns on the device when tissue contacts the electrodes.
Figures 1, 2B:
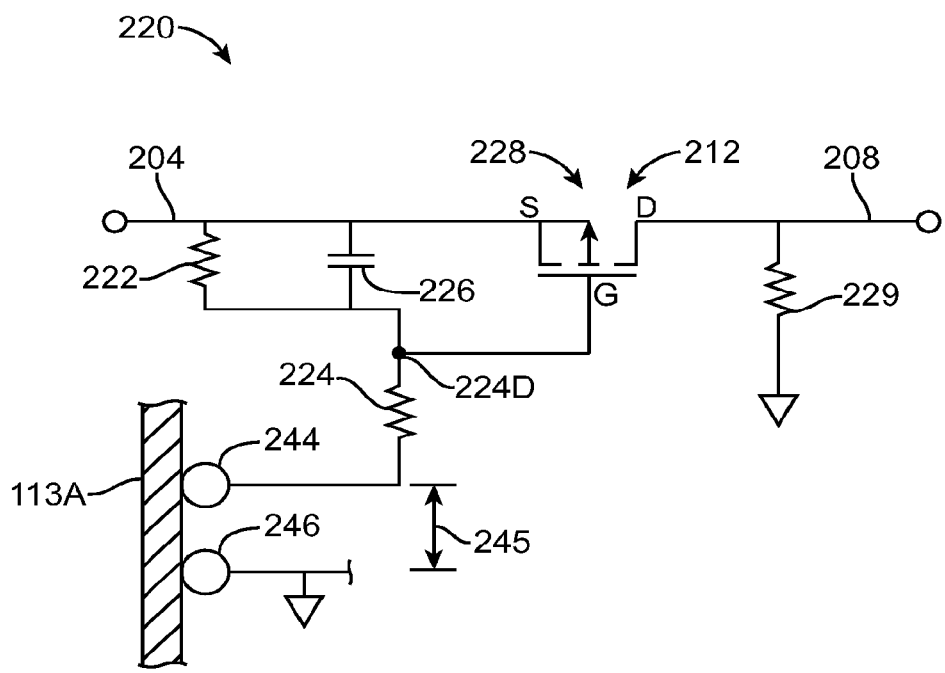

FIG. 2B shows additional detail of the start-up circuitry 220 of FIG. 2A that automatically turns on components of circuitry 200 when tissue contacts the electrodes. Start-up circuitry 220 can be connected to output 204 of battery 202. Start-up circuitry 220 comprises a transistor, for example a p-channel FET transistor 228. Transistor 228 comprises a switch that can be opened and closed in response to tissue contact to the electrodes. Transistor 228 comprises a gate G, such that current flow through transistor 228 is inhibited while voltage to gate G remains above a threshold voltage. When tissue does not contact electrodes 244 and 246, voltage to gate G is above the threshold voltage and current flow through transistor 228 is inhibited. Start-up circuitry 220 comprises resistor 222 and resistor 224. A capacitor 226 can be disposed in parallel to resistor 222.

When tissue T is coupled to, for example contacts, electrode 244 and electrode 246, current can flow through tissue T because gate G of transistor 228 is driven below the threshold voltage. In some embodiments, electrode 244 and electrode 246 may comprise know gels, for example hydrogels, to couple to the skin of a patient. Resistor 222 and resistor 224 are connected in series so as to form a voltage divider having an output 224D. Tissue T comprises a resistance that is much lower that resistor 222 and resistor 224. Resistor 222 comprises a resistance, for example 100 MΩ, that is much greater than a resistance of resistor 224, for example 1 MΩ. Resistor 222 comprises a resistance much greater than the resistance of tissue T. When tissue is connected across electrode 244 and electrode 246, current flows across the voltage divider from battery 202 to electrode 246 which is connected to ground. Thus, the voltage to gate G from the divider is driven substantially below the threshold value, such that the transistor switch closes and current can flow through transistor 228 to input 208 of voltage regulator 206. Capacitor 226 can delay switching for an amount of time after tissue contacts the electrodes, for example in response to an RC time constant of capacitor 226 and resistor 222. A high impedance resistor 229 can be provided to measure a signal voltage to input 208 to voltage regulator 206.

Start-up circuitry 220 can be configured such that the pre-determined threshold impedance of tissue corresponds to the voltage threshold of transistor 228 comprising the switch. For example, resistor 222 and resistor 224 of the voltage divider can be selected such that the voltage to gate G is driven to the threshold voltage, for example an FET switching voltage, so as to close the transistor switch when the impedance across the electrodes comprises a desired pre-determined tissue threshold impedance at which the switch is intended to close. Known circuit modeling methods can be used to determine the appropriate values of the gate threshold, resistors and capacitors so as to close the at least one switch when the impedance across the electrodes corresponds to the threshold tissue detection impedance.

Electrodes 244 and 246 can be separated by a distance 245. Distance 245 may be dimensioned so that electrodes 244 and 246 can detect tissue contact and make tissue measurements, as described above.

When circuitry 200 is configured for use with an implantable device, one of the at least two electrodes may comprise a housing of the device that contacts tissue.

FIG. 2B-1 shows the start-up circuitry of FIG. 2B with a liner, for example liner 113A coupled to the electrodes. Liner 113A comprises an impedance greater than tissue, such that the start-up circuitry is not activated and the at least one switch remains open when the liner is coupled to the at least two electrodes, for example electrode 244 and electrode 246. The liner can be coupled to the electrodes in many ways, for example with direct contact of liner 113 A to electrode 244 and electrode 246. The liner can also be coupled to the electrodes with a gel, for example with a gel pad disposed on each electrode between the liner and the electrode such that the gel pads remain separated when the liner is placed over the electrodes, as described above. The gel pads may comprise a solid material, such that the gel pads do not contact each other when the device is adhered to the patient. The gel pads may comprise a solid gel, and may comprise internal structures such as a scrim, mesh, or scaffold, to retain the shape and separation of the gel pads.

The impedance of liner 113A, for example the resistance, is determined by the material properties of liner 113A, and also by the distance 245 between electrode 244 and electrode 246. An example of a relevant material property of the liner is the resistivity of the material, $\rho$. The resistivity is inversely proportional to the conductivity of the material, $\sigma$, which is given by $1/\rho$. In some embodiments, the resistivity of the material is substantially determined by the measured resistance, R, times the cross sectional area A, divided by the length L between electrodes. For example, an increase in distance 245 can increase the resistance of the liner between the electrodes. An increase in cross-sectional area of the liner between the electrodes can decrease the resistance of the liner between the electrodes. For example, an increase in thickness of the liner may increase the cross sectional area of the liner between the electrodes so as to decrease the resistance. Similarly, and increase in the width of the liner, for example width 174, as described above, may decrease the resistance of the liner between the electrodes. In many embodiments, the thickness of the liner may comprise no more than about 1 mm, such the resistance of the liner minimizes current flow through the liner when the liner is placed over and/or coupled to the electrodes. In many embodiments, the electrodes are separated to provide a desired predetermined impedance, for example resistance, based on the thickness and material properties of the liner.

The liner thickness, material properties and electrode spacing can be configured to provide the desired liner resistance between electrode 244 and electrode 246 when the liner is coupled to the electrodes, for example coupled with a gel pad disposed between the liner and each electrode. For example the liner resistance comprises at least 1 MΩ, for example at least 10 MΩ, or even 100 MΩ. In many embodiments, at least one of the liner conductivity, the liner thickness, the liner width or the electrode spacing are configured to provide the resistance between the electrodes, for example a resistance of at least 100 MΩ, for example 1 GΩ (1000 MΩ). Therefore, the liner and electrode spacing can be configured to minimize current flow through the liner and degradation to the electrodes when the device is stored with power to the start-up circuitry 220 for an extended period of at least one month, for example at least 3 months. For example, with a liner configured for 3 GΩ impedance between the electrodes and 3 volts to the start-up circuitry, the current flow through electrode 244 and electrode 246 is about 1 nA. In another example, the current flow through the electrode 244 and electrode 246 is about 15 nA, for a 3V battery, a liner having a resistance of about 100 MΩ between electrode 244 and electrode 246, resistor 222 having a resistance of about 100 MΩ, and resistor 224 having a resistance of about 1 MΩ.

The resistivity of the liner material may comprise at least about 5 kΩ-m. For example, PET has a resistivity of about $10^{20}$ Ω-m, hard rubber about $10^{13}$ Ω-m, and silicone about 240 M Ω-m. In a specific embodiment with a liner thickness of 1 mm, a width of 50 mm and a separation distance between electrodes of 100 mm, a liner material resistivity of about 5 kΩ-m can provide a resistance between electrodes about 10 M-Ω.

Figure 2C:
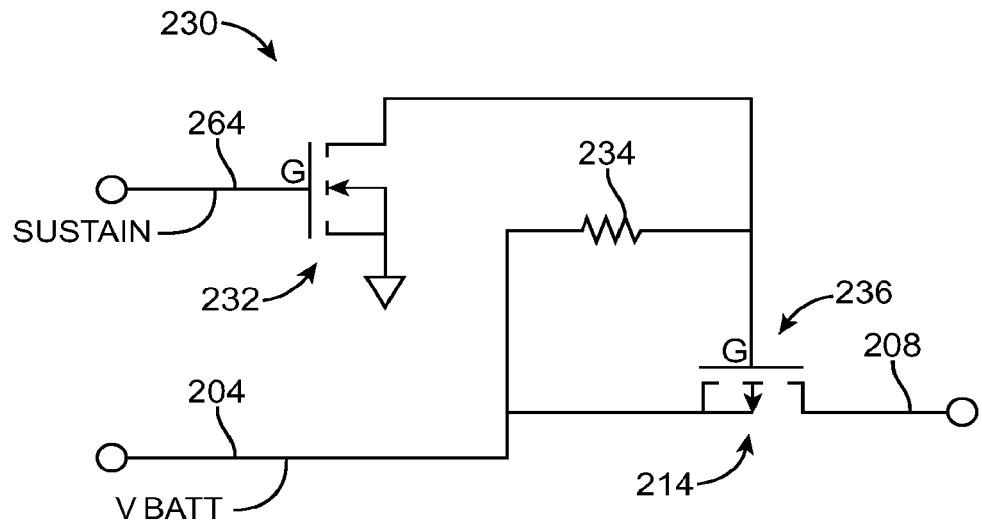
FIG. 2C shows additional detail of the sustain circuitry of FIG. 2A that sustains power from the battery to the voltage regulator after the tissue is removed from the electrodes and allows the processor to turn the device off after tissue is removed from the electrodes.
Figure 2D:
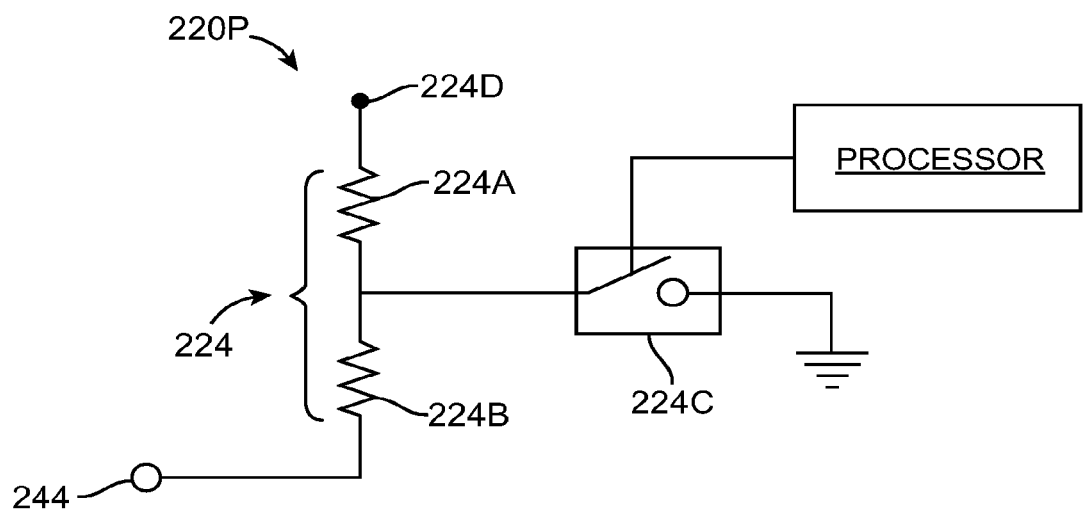
FIG. 2D shows circuitry to decrease parasitic current flow through the electrodes coupled to the tissue detection circuitry when tissue is coupled to the electrodes.
Figure 2E:
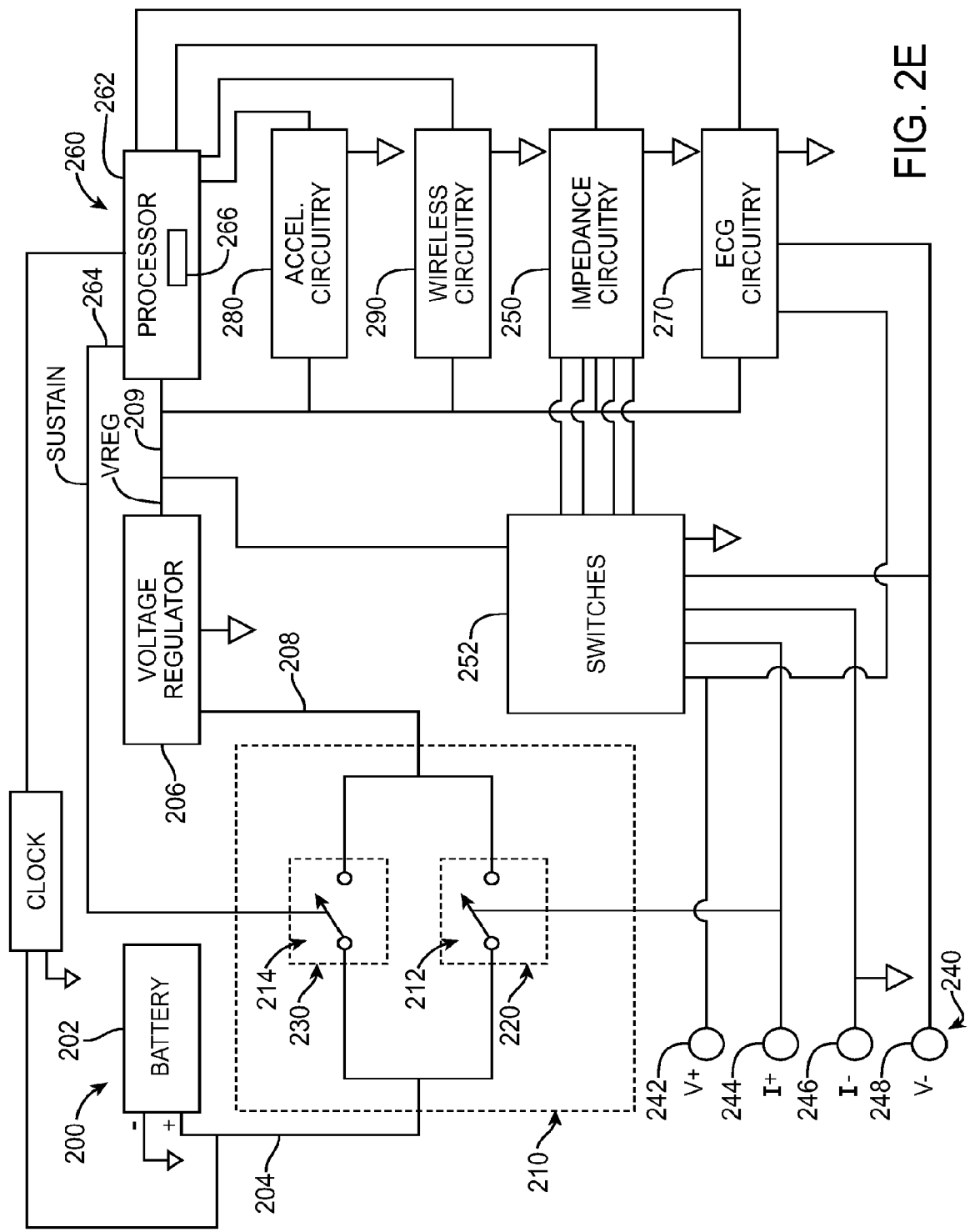
FIG. 2E shows a clock coupled to the battery to determine the current date and time when the circuit for automatically turning on the device is open.

FIG. 2E shows a load that is connected to the battery when the circuitry for automatically turning on the device is open. For example the load may comprise a clock coupled to the battery to determine the current date and time when the circuit for automatically turning on the device is open. The clock is coupled to the battery to draw power when the at least one switch is open, and the voltage regulator and processor are decoupled from the battery. Thus, the clock draws power to determine the date and time when the device is in the low power configuration, such that the clock can be set at the factory with the date and time when the battery is installed. The clock is coupled to the processor so that the data collected with the sensor circuitry can be date and time stamped when processor draws power and the data are measured. The amount of current used by the load, for example the clock, may comprise no more that about 1 uA, for example no more than about 0.5 uA. Therefore, the device is ready for use with the correct time upon activation of the sensor circuitry when the electrodes are coupled to the patient tissue.

FIG. 2C shows additional detail of the sustain circuitry 230 of FIG. 2A. Sustain circuitry 230 sustains power from the battery to the voltage regulator after tissue is removed from the electrodes, and allows the processor to turn the device off after the tissue is removed from the electrodes. Sustain circuitry 230 comprises a switch, for example a p-channel FET transistor 236, disposed in series between output 204 of battery 202 and input 208 of regulator 206.

Before tissue contacts the electrodes, gate G of transistor 236 is high so that the switch is open and battery 202 is disconnected from voltage regulator 206. One will appreciate that transistor 228 is in parallel transistor 236, such that no current can flow from battery 202 to regulator 206 when both switches are open. Thus, in the initial condition prior to tissue contact to the electrodes, and battery 202 is disconnected from regulator 206. In this initial condition, no power is supplied to regulator 206, such that processor 262 receives no power and control line 264 comprises a low voltage signal. Control line 264 is connected to a gate of transistor switch, for example an n-channel FET transistor 232, such that the switch is open when gate G is below the threshold voltage of the gate. Before the processor is activated control line 264 comprises a low voltage signal that is below the threshold of transistor 232, the switch is open and no substantial current flows through transistor 232. Thus, in the initial condition prior to tissue contacting the electrodes, control line 264 comprises a low voltage signal and no substantial current flows through transistor 232, and gate G of transistor 236 comprises a high voltage such that the switch is open.

When tissue contacts the electrodes, at least one switch 212 of start-up circuitry 220 closes and processor 262 receives power from voltage regulator 206. Processor 262 comprises a tangible medium configured to close at least one switch 212 of sustain circuitry 230 when processor 262 is activated, such that battery 202 is connected to voltage regulator 206. Processor 262 can assert a high voltage signal on control line 264 when the processor boots up, such that gate G of transistor 232 receives a high voltage signal and the switch closes. Current through transistor 232 will also pass through resistor 234 and lower the voltage at gate G of transistor 236 below the threshold voltage, such that current passes through transistor 236 and at least one switch 214 is closed. Thus, output 204 of battery 202 remains connected to input 208 of voltage regulator 206 while processor 262 maintains a high voltage signal on control line 264 such that processor 262 sustains the connection of the battery to the voltage regulator with at least one switch 214.

Once tissue has been disconnected from the electrodes, at least one switch 212 of start-up circuitry 220 opens and the processor can execute the shut down process. After the tissue is disconnected from the electrodes, gate G of transistor 228 goes above the threshold voltage and current through the transistor is inhibited such the at least one switch 212 comprises open configuration, and battery 202 is not connected to voltage regulator 206 through the at least one switch 212 of start-up circuitry 220. In this configuration, voltage regulator 206 receives power from battery 202 through at least one switch 214 of sustain circuitry 230 that is in parallel to at least one switch 212 of start-up circuitry 220. When processor 262 asserts command line 264 to a low voltage signal in response to commands stored in processor memory, battery 202 is disconnected from voltage regulator 206 and the processor executes the shutdown process. In addition, the components of circuitry 200 that receive power from voltage regulator 206 are also disconnected from battery 202 and turned off.

One will recognize that the start-up circuitry described herein can be incorporated with many known devices and/or electrodes, for example implantable and/or injectable devices as described in U.S. Pub. Nos. 2007/0162089; 2007/0092862; 2006/0195039; and 2005/0027204; 2005/0027175; and U.S. Pat. Nos. 7,118,531; 6,936,006; and 6,185,452.

FIG. 2D shows circuitry 220P to decrease parasitic current flow through the electrodes coupled to the tissue detection circuitry when tissue is coupled to the electrodes. Circuitry 220P can also sustain voltage to the regulated power supply, microprocessor and other components that wake upon tissue contact, similar to the sustain circuitry described above. Resistor 222 and resistor 224 comprise a voltage divider 224D, as noted above. Resistor 224 may comprise a pair of resistors, for example a first resistor 224A and a second resistor 224B. A switch 224C is coupled to the voltage divider and to ground, such that when switch 224C is closed the output 224D of the voltage divider is driven low, for example substantially to ground. Switch 224C is coupled to the processor, as above, such that the processor can open and close switch 224C in response to commands from the processor.

Switch 224C can be connected to resistor 224 between resistor 224A and resistor 224B to pull output 224D to a low state, for example substantially grounded. Resistor 224B may comprise most of the resistance of resistor 224, for example at least 80%, or even 90%, such that when the processor closes switch 224C, output 224D is substantially grounded. As noted above, resistor 222 comprises a resistance, for example 100 MΩ, that is much greater than a resistance of resistor 224, for example 1 MΩ. Resistor 222 comprises a resistance much greater than the resistance of tissue T. Thus, when switch 224C closes, output 224D comprises a low voltage state.

As switch 224C is coupled to the voltage divider comprises resistor 222 and resistor 224 so as to shunt the current passing through resistor 222 to ground. Resistor 222 comprises substantially more resistance than resistor 224, such that when output switch 224C is closed and output 222D is low most of the current through resistor 222 is shunted to ground instead of through electrode 244 and electrode 246. Consequently parasitic current flow through electrode 244 and electrode is minimized. This minimization of the current flow through electrode 244 and electrode 246 may decrease degradation of the electrodes, for example from oxidation, and may increase the useful life of the electrodes when the electrodes contact the tissue.

To detect removal of tissue coupling from the electrodes, the processor can be configured to poll the tissue detection circuitry. For example the processor open switch 224C and measure the output voltage of the tissue detection circuit to determine if tissue has been removed from the electrodes. The processor can then close switch 224C to shunt the current to ground. These polling steps can be repeated at regular intervals, for example once per minute, to determine if the adherent device has been removed from tissue so as to decouple the electrodes from the skin of the patient.

Figure 3:
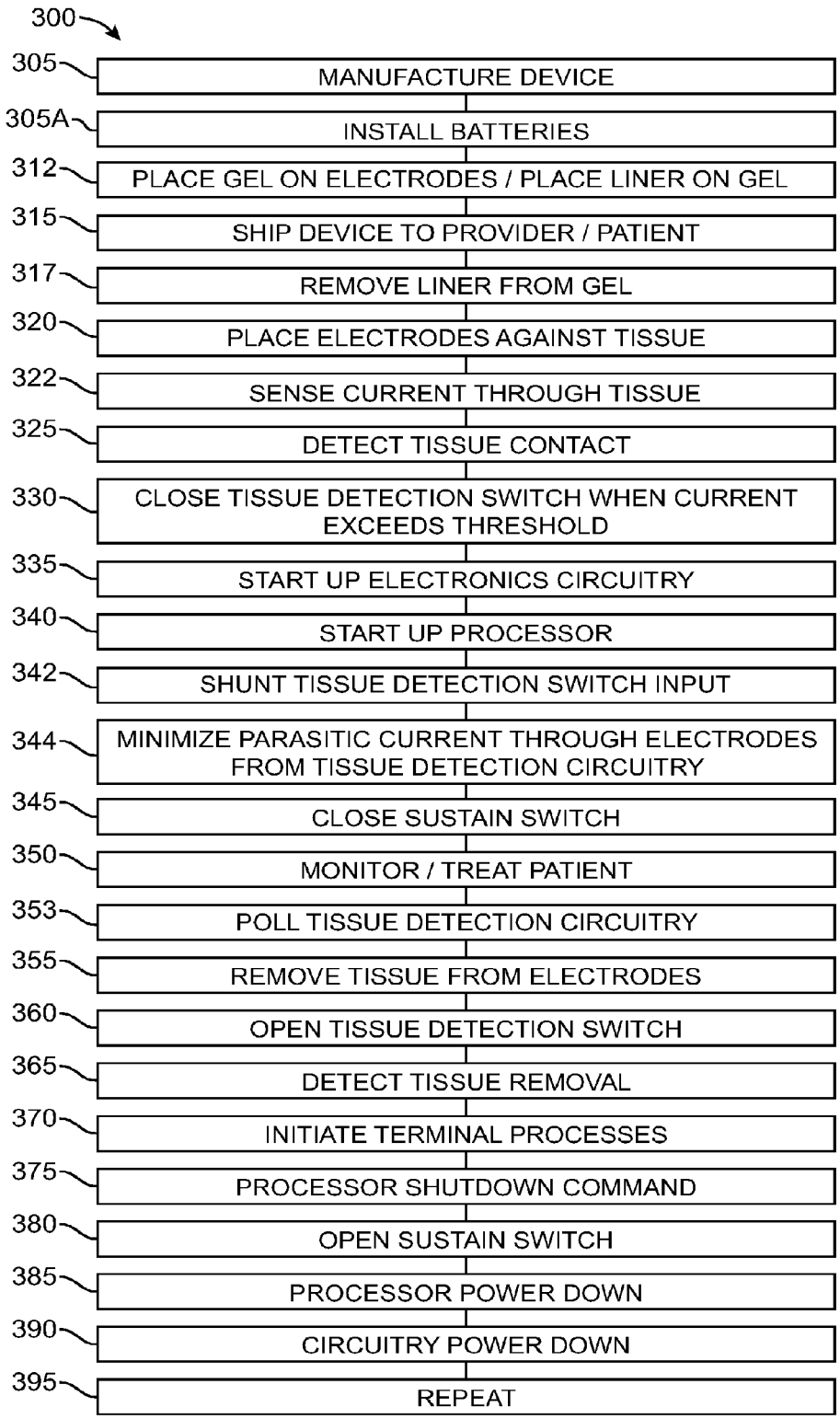
FIG. 3 shows a method of monitoring and/or treating a patient with a medical device that automatically turns on in response to patient tissue contact, according to embodiments of the present invention.

FIG. 3 shows a method 300 of monitoring and/or treating a patient with a medical device, which automatically turns on in response to patient tissue contact. A step 305 manufactures the device. The device may comprise at least two electrodes and energy storage cells, for example batteries, that are used to power the device. A sub-step 305A installs batteries in the device. A step 312 places a gel over the electrodes and places a liner over the gel. The batteries can be installed at the factory as part of the manufacturing process. A step 315 ships the device from the factory to the health care provider and/or patient. A step 317 removes the liner from the gel. A step 320 places the gel covered electrodes against the patient tissue. The electrodes may comprise stimulation electrodes and/or measurement electrodes to measure biological signals from tissue. The contact of the tissue many comprise contact with the skin to the electrode and/or contact with an internal tissue, for example cardiac tissue that contacts a pacing lead. A step 322 senses current through the contact with the skin and/or tissue. A step 325 detects contact of the tissue to the electrodes. The tissue can be detected with at least one switch, as described above. A step 330 closes the tissue detection switch, for example the at least one switch that connects a battery to a voltage regulator as described above. The tissue detection switch closes when the current passed through the tissue exceeds a predetermined threshold current. A step 335 starts up the electronics circuitry, with power from the closed switch. A step 340 starts up, or boots up, a processor as described above. A step 342 shunts the tissue detection switch input. For example the processor may close a switch coupled to ground such that the output of a voltage divider is substantially 0, as described above. A step 344 minimizes parasitic current through the electrodes coupled to the tissue detection circuit, for example as described above. A step 345 closes a sustain power switch that sustains power to the processor, for example with at least one switch as described above. A step 350 monitors and/or treats the patient, for example with at least one of accelerometers, impedance measurements, ECG measurements, and/or wireless transmission of data, for example to a remote center. A step 353 polls the tissue detection circuitry to determine if the tissue has been removed from the electrodes, for example as described above. A step 355 removes tissue from the electrodes. A step 360 opens a tissue detection switch in response to removal of the tissue from the electrodes. For example, at least one tissue detection switch, as described above, can open in response to removal of the tissue from the electrodes. A step 365 detects tissue removal, for example with a signal from a line connected to the processor, as described above. A step 370 initiates terminal processes in response to detection of removal of the tissue. For example, the processor can transmits patient measurement data to a remote center and/or a signal that the patient has removed the device in response to the tissue removal signal. A step 375 initiates a processor shutdown command. The processor shutdown command can be initiated after the terminal processes have been completed, such that the desired signals can be completely transmitted before the processor issues the shutdown command. A step 380 opens the sustain switch in response to the processor shutdown command. A step 385 powers down the processor in response to the sustain switch opening. A step 390 power down additional associated circuitry in response to the sustain switch opening. A step 395 can repeat the above steps. Repetition of at least some of the above steps can be desirable with a device in which the processor and measurement circuitry can be re-attached to the patient while the electrodes and adherent patch are disposed of after use. In some embodiments, a re-usable electronics module that can be coupled to disposable adherent patches, as described in U.S. App. No. 60/972,537, filed Sep. 14, 2007, the full disclosure of which is incorporated herein by reference. In some embodiments, the processor can execute the shutdown process to reduce power consumption when the device is removed from the patient, and subsequent re-attachment of the device to the patient can start-up the measurement and/or processor circuitry when the device is re-attached to the patient, thereby minimizing power consumption when the device is removed from the patient.

It should be appreciated that the specific steps illustrated in FIG. 3 provide a particular method of monitoring and/or treating a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 3 may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A device for monitoring or treating a patient, the device comprising: a battery; circuitry configured to at least one of monitor or treat the patient, the circuitry comprising a processor; at least two electrodes configured to couple to tissue of the patient; a first switch coupled to the at least two electrodes, the battery and the circuitry, and wherein the first switch is configured to detect tissue coupling to the at least two electrodes and connect the battery to the circuitry in response to tissue coupling to the at least two electrodes; and a shunt switch coupled to the first switch and controlled by the processor to minimize parasitic current through the at least two electrodes coupled to the tissue detection circuitry, wherein the processor is configured to open the shunt switch at regular intervals to determine if the device has been removed from the patient.

2. The device of claim 1, wherein the shunt switch is closed by the processor to decrease parasitic current through the at least two electrodes.

3. The device of claim 1, wherein the shunt switch is opened by the processor to allow the first switch to detect whether the at least two electrodes are coupled to tissue.

4. The device of claim 1, wherein the first switch comprises a voltage divider and a transistor having a gate with a threshold voltage and wherein the voltage divider and the threshold voltage are configured to close the first switch when an impedance between the at least two electrodes is below a threshold tissue detection impedance.

5. The device of claim 4, wherein the voltage divider includes a first resistor, a second resistor, a third resistor and an output connected to the gate of the transistor, wherein the first resistor is connected between the battery and the output and the second resistor is connected between the output and one of the at least two electrodes.

6. The device of claim 5, wherein the shunt switch is connected to a node located between the third and fourth resistors and ground, wherein closing the shunt switch results in the output of the voltage divider being pulled low.

7. The device of claim 6, wherein the resistance of the second resistor is much smaller than the resistance of the third resistor.

8. The device of claim 1, further comprising sustain circuitry comprising a second switch to connect the battery to the processor in response to a signal from the processor, such that power is sustained to the processor after the tissue is uncoupled from the at least two electrodes and the first switch opens.

9. The device of claim 8, further comprising a voltage regulator, wherein the first switch and the voltage regulator are connected in series between the battery and the circuitry to at least one of monitor or treat the patient, such that the first switch and the voltage regulator connect the battery to the circuitry to at least one of monitor or treat the patient.

10. A method of monitoring and/or treating a patient with a device having a battery, circuitry to monitor and/or treat the patient, at least two electrodes configured to couple to skin of the patient, a first switch and a shunt switch, the method comprising:
    contacting the electrodes with tissue of the patient;
    detecting contact of the electrodes with tissue of the patient, wherein the first switch is coupled to detect a change of resistance resulting from contact of the electrodes with tissue of the patient;
    closing the first switch in response to the detected contact of the electrodes with tissue of the patient to provide power from the battery to the monitoring and/or treatment circuitry via the first switch;
    providing a control signal from the monitoring and/or treatment circuitry to the shunt switch to close the shunt switch to minimize parasitic current through the at least two electrodes; and
    periodically providing a control signal from the monitoring and/or treatment circuit to open the shunt switch to allow detecting of contact of the electrodes with tissue of the patient by the first switch.

11. The method of claim 10, further comprising closing a second switch connected in parallel with the first switch between the battery and the monitoring and/or treatment circuitry, wherein the second switch is closed in response to a sustain signal provided by the monitoring and/or treatment circuit.

12. The method of claim 11, wherein the second switch remains closed such that power is sustained to the monitoring and/or treatment circuitry after the electrodes are removed from the tissue of the parent and detected by the first switch, resulting in the first switch being opened.

13. The method of claim 12, further comprising sending a signal to a remote center in response to the electrodes being removed from the tissue, wherein the monitoring and/or treatment circuitry receives power via the second switch following the electrodes being removed from the tissue.

14. The method of claim 12, further comprising initiating a shutdown operation in response to the electrodes being removed from the tissue, wherein the monitoring and/or treatment circuitry receives power via the second switch following the electrodes being removed from the tissue.

15. The method of claim 14, wherein the monitoring and/or treatment circuitry opens the second switch to remove power from the monitoring and/or treatment circuitry following completion of the shutdown operation.

* * * * *